United States Patent
Schneider et al.

(10) Patent No.: US 6,864,330 B2
(45) Date of Patent: Mar. 8, 2005

(54) USE OF HYDROPHILIC GRAFT COPOLYMERS CONTAINING N-VINYLAMINE AND/OR OPEN-CHAIN N-VINYLAMIDE UNITS IN COSMETIC FORMULATIONS

(75) Inventors: Tanja Schneider, Bensheim (DE); Michael Gotsche, Mannheim (DE); Anton Negele, Deidesheim (DE); Son Nguyen Kim, Hemsbach (DE); Stefan Frenzel, Mannheim (DE); Claudia Wood, Weinheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/362,053
(22) PCT Filed: Aug. 17, 2001
(86) PCT No.: PCT/EP01/09491
§ 371 (c)(1), (2), (4) Date: Feb. 20, 2003
(87) PCT Pub. No.: WO02/15854
PCT Pub. Date: Feb. 28, 2002

(65) Prior Publication Data
US 2003/0199642 A1 Oct. 23, 2003

(51) Int. Cl.$^7$ .................. C08F 283/00; C08F 28/12
(52) U.S. Cl. ................... 525/479; 525/205; 525/191; 523/105
(58) Field of Search ................... 525/479, 205, 525/191; 523/105

(56) References Cited

U.S. PATENT DOCUMENTS

| 5,270,379 A | 12/1993 | McAndrew et al. |
| 5,334,287 A | 8/1994 | Hartmann et al. |
| 5,753,759 A | 5/1998 | Hartmann et al. |
| 6,048,945 A | 4/2000 | Denzinger et al. |
| 6,191,215 B1 * | 2/2001 | Beckham et al. ........... 524/731 |
| 6,231,876 B1 | 5/2001 | Niessner et al. |
| 6,248,836 B1 | 6/2001 | Negele et al. |
| 6,362,245 B1 * | 3/2002 | Takahashi et al. .......... 521/149 |

FOREIGN PATENT DOCUMENTS

| DE | 1 495 692 | 11/1969 |
| DE | 44 09903 | 9/1995 |
| DE | 196 40363 | 4/1998 |
| DE | 199 07587 | 8/2000 |
| EP | 408 311 | 1/1991 |
| EP | 558 423 A1 | 9/1993 |
| EP | 558 423 B1 | 9/1993 |
| EP | 629 649 | 12/1994 |
| EP | 0931 537 | 7/1999 |
| GB | 1044956 | 10/1966 |
| WO | 95/21880 | 8/1995 |
| WO | 96 03969 | 2/1996 |
| WO | 96/34903 | 11/1996 |
| WO | 98/25981 | 6/1998 |

OTHER PUBLICATIONS

Griffin, Calculation of HLB Values of non–ionic surfactants 249–256,J. Soc.of Cosm.Chemists, 1954.

Fikentscher, Systematik der Cellulosen auf Grund inhrer Viskositat in Losung, 58–63; 71–74.

* cited by examiner

Primary Examiner—Kuo-Liang Peng
(74) Attorney, Agent, or Firm—Keil & Weinkauf

(57) ABSTRACT

The invention relates to the use of graft copolymers obtained by radical graft copolymerisation of a) at least one open-chained N-vinylamide compound of general formula (I) wherein $R^1$, $R^2$, $R^3$ represents H or $C_1$–$C_6$-alkyl and b) optionally, one or several other copolymerizeable monomers on a polymer graft base c) for cosmetic applications, with the proviso that if the polymer graft base is a compound containing polyether, the copolymerizeable polymer b) does not represent vinylester (I)

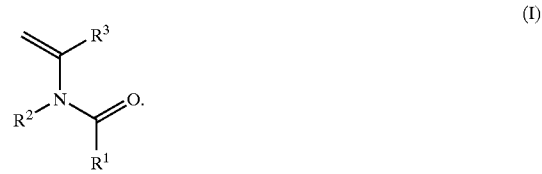

18 Claims, No Drawings

USE OF HYDROPHILIC GRAFT COPOLYMERS CONTAINING N-VINYLAMINE AND/OR OPEN-CHAIN N-VINYLAMIDE UNITS IN COSMETIC FORMULATIONS

The invention relates to the use of graft copolymers as a constituent in cosmetic compositions. The graft copolymers arise here as a result of grafting monoethylenically unsaturated, open-chain monomers containing N-vinylamide units to a polymeric graft base.

Polymers are used widely in cosmetics and medicine. In soaps, creams and lotions, for example, they usually serve as formulation agents, e.g. as thickeners, foam stabilizers or water absorbents, or else for alleviating the irritative action of other ingredients, or for improving the dermal application of active ingredients. By contrast, their task in hair cosmetics is to influence the properties of the hair.

For example, conditioners are used for improving the dry and wet combability, feel, shine and appearance, and for imparting antistatic properties to the hair. Preference is given to using water-soluble polymers with polar, frequently cationic functionalities which have a greater affinity to the surface of the hair, which is negative as a result of its structure. The structure and mode of action of various hair-treatment polymers are described in Cosmetic & Toiletries 103 (1988) 23. Commercially available conditioning polymers are, for example, cationic hydroxyethylcellulose, cationic polymers based on N-vinylpyrrolidone, e.g. copolymers of N-vinylpyrrolidone and quaternized N-vinylimidazole, acrylamide and diallyldimethylammonium chloride or silicones.

For setting hairstyles, use is made of vinyllactam homopolymers and copolymers and polymers containing carboxylate groups. Requirements for hair-setting resins are, for example, a strong hold at high atmospheric humidity, elasticity, wash-off from the hair, compatibility in the formulation and a pleasant feel of the hair.

The combination of different properties, such as, for example, strong hold and pleasant feel of the hair, often presents difficulties.

WO-A-96/03969 describes haircare compositions comprising an N-vinylformamide homopolymer or a copolymer of N-vinylformamide units and a further vinyl monomer chosen from styrenes, alkyl esters of acrylic and methacrylic acid, vinyl esters of the formula $CH_2=CH-OCO$-alkyl, N-alkyl-substituted acrylamides and methacrylamides, esters of fumaric, itaconic and maleic acid, vinyl ethers, hydroxy-functionalized acrylates and methacrylates, acrylamides, non-alkyl-substituted acrylamides and cyclic amides. A specific example of a cyclic amide is N-vinylpyrrolidone. Further examples of vinyl monomers are secondary, tertiary and quaternary amines, such as dimethyldiallylammonium chloride, dimethylaminoethyl methacrylate or dimethylaminopropyl methacrylate.

DE 19640363 describes copolymers of N-vinylformamide and quaternized N-vinylimidazole and the uses thereof in cosmetics.

DE 19907587.5 describes the use of polymers obtainable by free-radical polymerization of at least one vinyl ester in the presence of polyether-containing compounds and optionally one or more copolymerizable monomers, and subsequent at least partial saponification of the ester function in hair cosmetic formulations. A copolymerizable monomer is, inter alia, vinylformamide.

DE-A1-44 09 903 describes graft polymers containing N-vinyl units, processes for their preparation and their use.

Here, monoethylenically unsaturated monomers are grafted on to a graft base which is a polymer which in each case contains at least 5% by weight of units of the formulae

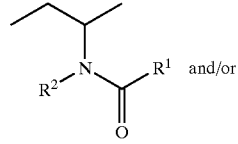

(IV)

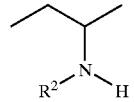

(V)

where $R^1$, $R^2$=H or $C_1$–$C_6$-alkyl. Suitable monoethylenically unsaturated monomers are all ethylenically unsaturated monomers whose polymerization is not inhibited by the amine groups in free or in salt form, such as, for example, monoethylenically unsaturated mono- and dicarboxylic acids, their salts and esters with $C_1$–$C_{30}$-alcohols. Suitability of these graft copolymers as active ingredient in cosmetic formulations is not mentioned.

WO 96/34903 describes graft polymers containing N-vinyl units, processes for their preparation and their use. Here, monoethylenically unsaturated monomers are grafted onto a graft base which is a polymer which contains at least 3 units of a $C_2$–$C_4$-alkylene oxide, and/or polytetrahydrofuran, and then at least partially saponified. Suitability of these graft copolymers as active ingredient in cosmetic formulations is not mentioned.

U.S. Pat. No. 5,334,287 discloses graft polymers obtainable by free-radical-initiated polymerization of N-vinylcarboxamides, preferably N-vinylformamide, and optionally other monomers in the presence of monosaccharides, oligosaccharides, polysaccharides or derivatives thereof in each case, and optionally hydrolysis of the copolymerized N-vinylcarboxamide group to form vinylamine units. Suitability of these graft copolymers as active ingredient in cosmetic formulations is not mentioned.

In WO 9825981, amphiphilic graft polymers are synthesized by grafting hydrophobic monomers, such as, for example, styrene, onto polymers which contain structural elements of the formula (IV) and/or (V). The graft polymers obtained are used inter alia as additives in cosmetic formulations.

DE-A1-196 40 363 claims the use of water-soluble copolymers as active ingredient in cosmetic formulations. As a characteristic structural element, the copolymer contains units of the formula (VI)

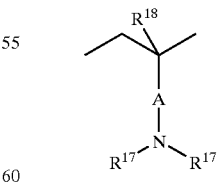

(VI)

in which A is a chemical bond or an alkylene group, the radicals $R^{17}$, independently of one another, are H, alkyl, cycloalkyl, aryl or aralkyl, and $R^{18}$ is H, alkyl or aralkyl.

Bodycare creams which contain a monoaldehyde-modified vinylamine polymer are known from U.S. Pat. No. 5,270,379.

Copolymers which are used, for example, as hair-setting agents and are built up from N-vinylamide monomers of the formula

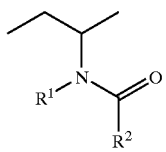

(V)

in which R1 and R2 are H or $C_1$–$C_5$-alkyl, and the comonomer is chosen from vinyl ethers, vinyllactams, vinylhalides, vinyl esters of monobasic saturated carboxylic acids, (meth) acrylic esters, amides and nitriles and esters, anhydrides and imides of maleic acid are known from DE 14 95 692.

U.S. Pat. No. 4,713,236 describes hair conditioners based on polymers containing vinylamine units. Particular mention is made here of polyvinylamine and salts thereof, α-substituted polyvinylamines, such as, for example, poly (α-aminoacrylic acid) and also copolymers which, in addition to vinylamine, contain, in copolymerized form, comonomers such as vinyl alcohol, acrylic acid, acrylamide, maleic anhydride, vinyl sulfonate and 2-acrylamido-2-methylpropanesulfonic acid.

It is an object of the present invention to find polymers which are highly suitable for cosmetic applications and which, for example in the field of hair cosmetics, have good applications-related properties, such as a pleasant feel, and at the same time good conditioning action and a good setting action.

We have found that this object is achieved according to the invention by the use of hydrophilic graft copolymers obtainable by free-radical graft copolymerization of a) at least one open-chain N-vinylamide compound of the formula (I)

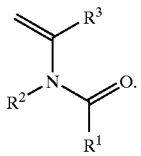

(I)

where $R^1$, $R^2$, $R^3$=H or $C_1$–$C_6$-alkyl, and b) optionally one or more further copolymerizable monomers to a polymeric graft base c)

for cosmetic applications.

In the preparation of the polymers used according to the invention, it is possible for grafting onto the polymeric graft base c) to result during the polymerization, which may lead to advantageous properties of the polymers. However, mechanisms other than grafting are also conceivable.

Depending on the degree of grafting, the polymers used according to the invention are understood as meaning pure graft polymers and also mixtures of the abovementioned graft polymers with ungrafted compounds c) and homo- or copolymers of the monomers a) and b).

Water-soluble polymers should here be understood as meaning polymers which dissolve in water in an amount of at least 1 g/l at 20° C. Water-dispersible polymers should here be understood as meaning polymers which fragment into dispersible particles when stirred.

For the preparation of the polymers used according to the invention, the following monomers are, for example, used as open-chain N-vinylamide compound a) of the formula (I): N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide. From this group of monomers, preference is given to using N-vinylformamide.

It is of course also possible to copolymerize mixtures of the respective monomers from group a), such as, for example, mixtures of N-vinylformamide and N-vinylacetamide.

The polymeric graft base c) is preferably chosen from c1) polyether-containing compounds c2) polymers which contain, in copolymerized form, at least 5% by weight of vinylpyrrolidone units c3) polymers which contain at least 50% by weight of vinyl alcohol units c4) natural substances which contain saccharide structures.

The polyether-containing compounds c1) which may be used are either polyalkylene oxides based on ethylene oxide, propylene oxide, butylene oxide and further alkylene oxides, or polyglycerol. Depending on the nature of the monomer building blocks, the polymers contain the following structural units. —$(CH_2)_2$—O—, —$(CH_2)_3$—O—, —$(CH_2)_4$—O—, —$CH_2$—$CH(R^9)$—O—, —$CH_2$—$CHR^{10}$—$CH_2$—O— where $R^9$ is $C_1$–$C_{24}$-alkyl;

$R^{10}$ is hydrogen, $C_1$–$C_{24}$-alkyl, $R^9$—C(=O)—, $R^9$—NH—C(=O)—.

The structural units may either be homopolymers or random copolymers and block copolymers.

As polyethers (c1), preference is given to using polymers of the formula II having a molecular weight >300

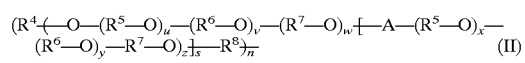

(II)

in which the variables, independently of one another, have the following meanings:

$R^4$ is hydrogen, $C_1$–$C_{24}$-alkyl, $R^9$—C(=O)—, $R^9$—NH—C(=O)—, polyalcohol radical;

$R^8$ is hydrogen, $C_1$–$C_{24}$-alkyl, $R^9$—C(=O)—, $R^9$—NH—C(=O)—;

$R^5$ to $R^7$ are —$(CH_2)_2$—, —$(CH_2)_3$—, —$(CH_2)_4$—, —$CH_2$—$CH(R^9)$—, —$CH_2$—$CHR^{10}$—$CH_2$—;

$R^9$ is $C_1$–$C_{24}$-alkyl;

$R^{10}$ is hydrogen, $C_1$–$C_{24}$-alkyl, $R^9$—C(=O)—, $R^9$—NH—C(=O)—;

A is —C(=O)—O, —C(=O)—B—C(=O)—O, —C(=O)—NH—B—NH—C(=O)—O;

B is —$(CH_2)_t$—, arylene, optionally substituted;

n is 1 to 1000;

s is 0 to 1000;

t is 1 to 12;

u is 1 to 5000;

v is 0 to 5000;

w is 0 to 5000;

x is 0 to 5000;

y is 0 to 5000;

z is 0 to 5000.

The terminal primary hydroxyl groups of the polyethers prepared on the basis of polyalkylene oxides, and the secondary OH groups of polyglycerol can in this connection either be present freely in unprotected form, or be etherified with alcohols of chain length $C_1$–$C_{24}$ or esterified with carboxylic acids of chain length $C_1$–$C_{24}$, or reacted with isocyanates to give urethanes.

Alkyl radicals which may be mentioned for $R^4$ and $R^8$ to $R^{10}$ are branched or unbranched $C_1$–$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$–$C_{12}$-, particularly preferably $C_1$–$C_6$-alkyl chains.

The molecular weight of the polyethers is at least 300 (according to number average), preferably in the range from 300 to 100 000, particularly preferably in the range from 500 to 50 000, very particularly preferably in the range from 800 to 40 000.

Homopolymers of ethylene oxide or copolymers with an ethylene oxide content of from 40 to 99% by weight are advantageously used. For the ethylene oxide polymers to be used in preference, the content of copolymerized ethylene oxide is thus from 40 to 100 mol %. Suitable comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content of the copolymers is preferably 40 to 99 mol %, the propylene oxide content is 1 to 60 mol % and the content of butylene oxide in the copolymers is 1 to 30 mol %. As well as straight-chain homo- or copolymers, it is also possible to use branched homo- or copolymers as polyether-containing compounds b).

Branched polymers can be prepared by, for example, adding ethylene oxide and optionally also propylene oxide and/or butylene oxides to polyalcohol radicals, e.g. to pentaerythritol, glycerol, or to sugar alcohols such as D-sorbitol and D-mannitol, but also to polysaccharides such as cellulose and starch. Within the polymer, the alkylene oxide units can be randomly distributed or be in the form of blocks.

It is, however, also possible to use polyesters of polyalkylene oxides and aliphatic or aromatic dicarboxylic acids, e.g. oxalic acid, succinic acid, adipic acid and terephthalic acid having molar masses of from 1 500 to 25 000, as described, for example, in EP-A-0 743 962, as polyether-containing compound. In addition, it is also possible to use polycarbonates by reaction of polyalkylene oxides with phosgene or carbonates such as, for example, diphenyl carbonate, and polyurethanes by reaction of polyalkylene oxides with aliphatic and aromatic diisocyanates.

Particularly preferred polyethers c1) are polymers of the formula II having an average molecular weight of from 300 to 100 000 (according to the number average), in which the variables, independently of one another, have the following meanings:

$R^4$ is hydrogen, $C_1$–$C_{12}$-alkyl, $R^9$—C(=O)—, $R^9$—NH—C(=O)—, polyalcohol radical;

$R^8$ is hydrogen, $C_1$–$C_{12}$-alkyl, $R^9$—C(=O)—, $R^9$—NH—C(=O)—;

$R^5$ to $R^7$ are —(CH$_2$)$_2$—, —(CH$_2$)$_3$—, —(CH$_2$)$_4$—, —CH$_2$—CH(R$^9$)—, —CH$_2$—CHOR$^{10}$—CH$_2$—;

$R^9$ is $C_1$–$C_{12}$-alkyl;

$R^{10}$ is hydrogen, $C_1$–$C_{12}$-alkyl, $R^9$—C(=O)—, $R^9$—NH—C(=O)—;

n is 1 to 8;

s is 0;

u is 2 to 2000;

v is 0 to 2000;

w is 0 to 2000.

Very particularly preferred polyethers c1) are polymers of the formula II having an average molecular weight of from 500 to 50 000 (according to the number average), in which the variables, independently of one another, have the following meanings:

$R^4$ is hydrogen, $C_1$–$C_6$-alkyl, $R^9$—C(=O)—, $R^9$—NH—C(=O)—;

$R^8$ is hydrogen, $C_1$–$C_6$-alkyl, $R^9$—C(=O)—, $R^9$—NH—C(=O)—;

$R^5$ to $R^7$ are —(CH$_2$)$_2$—, —(CH$_2$)$_3$—, —(CH$_2$)$_4$—, —CH$_2$—CH(R$^9$)—, —CH$_2$—CHOR$^{10}$—CH$_2$—;

$R^9$ is $C_1$–$C_6$-alkyl;

$R^{10}$ is hydrogen, $C_1$–$C_6$-alkyl, $R^9$—C(=O)—, $R^9$—NH—C(=O)—;

n is 1;

s is 0;

u is 5 to 500;

v is 0 to 500;

w is 0 to 500.

However, the polyethers used may also be silicone derivatives. Suitable silicone derivatives are the compounds known under the INCI name dimethicone copolyols or silicone surfactants, such as, for example, those available under the trade names Abil® (T. Goldschmidt), Alkasil® (Rhône-Poulenc), Silicone Polyol Copolymer® (Genesee), Belsil® (Wacker), Silwet® (Witco, Greenwich, Conn., USA) or Dow Corning (Dow Corning). These include compounds with the CAS numbers 64365-23-7; 68937-54-2; 68938-54-5; 68937-55-3.

Silicones are generally used in hair cosmetics to improve the feel. The use of polyether-containing silicone derivatives as polyethers (c1) in the polymers according to the invention can therefore additionally lead to an improvement in the feel of the hair.

Preferred representatives of such polyether-containing silicone derivatives are those which contain the following structural elements:

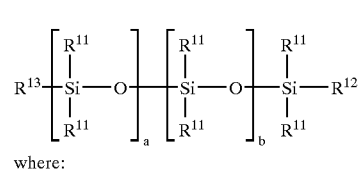

where:

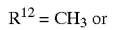

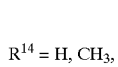

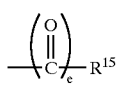

$R^{15}$ is a $C_1$–$C_{40}$ organic radical which can contain amino, carboxylic acid or sulfonate groups, or for the case e=0, is also the anion of an inorganic acid, and where the radicals $R^{11}$ may be identical or different, and either originate from the group of aliphatic hydrocarbons having 1 to 20 carbon atoms, are cyclic aliphatic hydrocarbons having 3 to 20 carbon atoms, are of an aromatic nature or are identical to $R^{12}$, where:

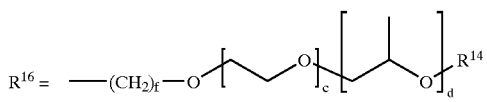

with the proviso that at least one of the radicals $R^{11}$, $R^{12}$ or $R^{13}$ is a polyalkylene-oxide-containing radical according to the abovementioned definition, and f is an integer from 1 to 6, a and b are integers such that the molecular weight of the polysiloxane block is between 300 and 30 000, c and d may be integers between 0 and 50, with the proviso that the sum of c and d is greater than 0, and e is 0 or 1.

Preferred radicals $R^{12}$ and $R^{16}$ are those in which the sum c+d is between 5 and 30.

The groups $R^{11}$ are preferably chosen from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals such as benzyl or phenylethyl and tolyl and xylyl and $R^{16}$.

Particularly suitable radicals $R^{14}$ are those in which in the case where $R^{14}$=—(CO)$_e$—$R^{15}$, $R^{15}$ is a desired alkyl, cycloalkyl or aryl radical which has between 1 and 40 carbon atoms and which can carry further ionogenic groups such as NH$_2$, COOH, SO$_3$H.

Preferred inorganic radicals $R^{15}$ are, for the case e=0, phosphate and sulfate.

Particularly preferred polyether-containing silicone derivatives are those of the structure:

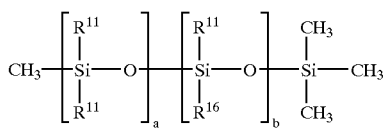

In addition, homo- and copolymers of polyalkylene-oxide-containing ethylenically unsaturated monomers, such as, for example, polyalkylene oxide (meth)acrylates, polyalkylene oxide vinyl ethers, polyalkylene oxide (meth) acrylamides, polyalkylene oxide allylamides or polyalkylene oxide vinylamides can also be used as polyethers (c1).

It is of course also possible to use copolymers of such monomers with other ethylenically unsaturated monomers.

As polyether-containing compounds c1), it is, however, also possible to use reaction products of polyethyleneimines with alkylene oxides. In this case, the alkylene oxides used are preferably ethylene oxide, propylene oxide, butylene oxide and mixtures thereof, particularly preferably ethylene oxide. Polyethyleneimines which can be used are polymers having number-average molecular weights of from 300 to 20 000, preferably from 500 to 10 000, very particularly preferably from 500 to 5 000. The weight ratio between used alkylene oxide and polyethyleneimine is in the range from 100:1 to 0.1:1, preferably in the range from 50:1 to 0.5:1, very particularly preferably in the range from 20:1 to 0.5:1.

As graft base, however, it is also possible to use polymers c2) which contain at least 5% by weight of vinylpyrrolidone units. Preferably, these polymers used as graft base contain a vinylpyrrolidone fraction of at least 10% by weight, very particularly preferably of at least 30% by weight.

Suitable as comonomers of the vinylpyrrolidone for the synthesis of the graft base (c2) are, for example, N-vinylcaprolactam, N-vinylimidazole, N-vinyl-2-methylimidazole, N-vinyl-4-methylimidazole, 3-methyl-1-vinylimidazolium chloride, 3-methyl-1-vinylimidazolium methyl sulfate, diallylammonium chloride, styrene, alkyl-styrenes.

Further suitable comonomers for the preparation of the graft base c2) are, for example, monoethylenically unsaturated $C_3$–$C_6$-carboxylic acids, such as, for example, acrylic acid, methacrylic acid, crotonic acid, fumaric acid, and esters, amides and nitriles thereof, such as, for example, methyl acrylate, ethyl acrylate, methyl methacrylate, ethyl methacrylate, stearyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, maleic anhydride and monoesters thereof, alkylene glycol (meth)acrylates, acrylamide, methacrylamide, N-dimethylacrylamide, N-tert-butylacrylamide, acrylonitrile, methacrylonitrile, vinyl ethers, such as, for example, methyl, ethyl, butyl or dodecyl vinyl ethers, cationic monomers, such as dialkylaminoalkyl (meth)acrylates and dialkylaminoalkyl (meth)acrylamides, such as dimethylaminoethyl acrylate, diethylaminoethyl acrylate, diethylaminoethyl methacrylate, and the salts of the last-named monomers with carboxylic acids or mineral acids, and the quaternized products.

The graft base is prepared by known processes, for example, solution, precipitation, suspension or emulsion polymerization using compounds which form free radicals under the polymerization conditions. The polymerization temperatures are usually in the range from 30 to 200, preferably 40 to 110° C. Suitable initiators are, for example, azo and peroxy compounds, and the customary redox initiator systems, such as combinations of hydrogen peroxide and compounds which have a reducing action, for example sodium sulfite, sodium bisulfite, sodium formaldehyde sulfoxilate and hydrazine. These systems may also additionally contain small amounts of a heavy metal salt.

The homopolymers and copolymers (graft base C2) have K values of at least 7, preferably 10 to 250. However, the polymers may have K values up to 300. The K values are determined in accordance with H. Fikentscher, Cellulose-Chemie, Volume 13, 58 to 64 and 71 to 74 (1932) in an aqueous solution at 25° C., at concentrations between 0.1% and 5% depending on the K value range.

As graft base, however, it is also possible to use polymers c3) which have at least 50% by weight of vinyl alcohol units. Preferably, these polymers contain at least 70% by weight, very particularly preferably 80% by weight, of polyvinyl alcohol units. Such polymers are usually prepared by polymerization of a vinyl ester and subsequent at least partial alcoholysis, aminolysis or hydrolysis. Preference is given to vinyl esters of linear and branched $C_1$–$C_{12}$-carboxylic acids, and very particular preference is given to vinyl acetate. The vinyl esters can of course also be used in a mixture.

Suitable as comonomers of the vinyl ester for the synthesis of the graft base (c3) are, for example, N-vinylcaprolactam, N-vinylpyrrolidone, N-vinylimidazole, N-vinyl-2-methylimidazole, N-vinyl-4-methylimidazole, 3-methyl-1-vinylimidazolium chloride, 3-methyl-1-vinylimidazolium methylsulfate, diallylammonium chloride, styrene, alkylstyrenes.

Further suitable comonomers for the preparation of the graft base c3) are, for example, monoethylenically unsaturated $C_3$–$C_6$-carboxylic acids, such as, for example, acrylic acid, methacrylic acid, crotonic acid, fumaric acid, and esters, amides and nitriles thereof, such as, for example, methyl acrylate, ethyl acrylate, methyl methacrylate, ethyl methacrylate, stearyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, maleic anhydride and monoesters thereof, alkylene glycol (meth)acrylates, acrylamide, methacrylamide, N-dimethylacrylamide, N-tert-butylacrylamide, acrylonitrile, methacrylonitrile, vinyl ethers, such as, for example, methyl, ethyl, butyl or dodecyl vinyl ethers, cationic monomers, such as dialkylaminoalkyl (meth)acrylates and dialkylaminoalkyl (meth)acrylamides, such as dimethylaminoethyl acrylate, diethylaminoethyl acrylate, diethylaminoethyl methacrylate, and the salts of the last-named monomers with carboxylic acids or mineral acids, and the quaternized products.

Preferably, graft bases c3) are polymers prepared by homopolymerization of vinyl acetate and subsequent at least partial hydrolysis, alcoholysis or aminolysis.

The graft base c3) is prepared by known processes, for example, solution, precipitation, suspension or emulsion polymerization using compounds which form free radicals under the polymerization conditions. The polymerization temperatures are usually in the range from 30 to 200, preferably 40 to 110° C. Suitable initiators are, for example, azo and peroxy compounds, and the customary redox initiator systems, such as combinations of hydrogen peroxide and compounds which have a reducing action, for example sodium sulfite, sodium bisulfite, sodium formaldehyde sulfoxilate and hydrazine. These systems may also additionally contain small amounts of a heavy metal salt.

For the preparation of the graft base c3), the ester groups of the original monomers and optionally of further monomers are at least partially cleaved after the polymerization by hydrolysis, alcoholysis or aminolysis. This process step is generally referred to below as saponification. The saponification is carried out in a manner known per se by adding a base or acid, preferably by adding a sodium or potassium hydroxide solution in water and/or alcohol. Particular preference is given to the use of methanolic sodium or potassium hydroxide solutions. The saponification is carried out at temperatures in the range from 10 to 80° C., preferably in the range from 20 to 60° C. The degree of the saponification depends on the amount of base or acid used, on the saponification temperature, the saponification time and the water content of the solution.

Particularly preferred graft bases c3) are polymers prepared by homopolymerization of vinyl acetate and subsequent at least partial saponification. Such polymers containing polyvinyl alcohol units are available under the name Mowiol®. As graft base, however, it is also possible to use natural substances c4) which contain saccharide structures. Such natural substances are, for example, saccharides of vegetable or animal origin or products formed by metabolization by microorganisms, and degradation products thereof. Suitable graft bases c4) are, for example, oligosaccharides, polysaccharides, oxidatively, enzymatically or hydrolytically degraded polysaccharides, oxidatively hydrolytically degraded or oxidatively enzymatically degraded polysaccharides, chemically modified oligo- or polysaccharides and mixtures thereof.

Preferred products are the compounds named in U.S. Pat. No. 5,334,287 in column 4, line 20 to column 5, line 45.

The preferred ethylenically unsaturated comonomers (b) additionally used can be described by the following formula:

where

X is chosen from the group of radicals —OH, —OM, —OR$^{21}$, NH$_2$, —NHR$^{21}$, N(R$^{21}$)$_2$;

M is a cation chosen from the group consisting of: Na$^+$, K$^+$, Mg$^{++}$, Ca$^{++}$, Zn$^{++}$, NH$_4^+$, alkylammonium, dialkylammonium, trialkylammonium and tetraalkylammonium;

the radicals R$^{21}$ can be identical or different and chosen from the group consisting of —H, $C_1$–$C_{40}$ linear or branched alkyl radicals, N,N-dimethylaminoethyl, 2-hydroxyethyl, 2-methoxyethyl, 2-ethoxyethyl, hydroxypropyl, methoxypropyl or ethoxypropyl.

R$^{20}$ and R$^{19}$ are, independently of one another, chosen from the group consisting of: —H, $C_1$–$C_8$ linear or branched alkyl chains, methoxy, ethoxy, 2-hydroxyethoxy, 2-methoxyethoxy and 2-ethoxyethyl.

Representative but nonlimiting examples of suitable monomers (b) are, for example, acrylic acid or methacrylic acid and salts, esters and amides thereof. The salts can be derived from any desired nontoxic metal, ammonium or substituted ammonium counterions.

The esters can be derived from $C_1$–$C_{40}$ linear, $C_3$–$C_{40}$ branched or $C_3$–$C_{40}$ carbocyclic alcohols, from polyfunctional alcohols having from 2 to about 8 hydroxyl groups, such as ethylene glycol, hexylene glycol, glycerol and 1,2,6-hexanetriol, from aminoalcohols or from alcohol ethers such as methoxyethanol and ethoxyethanol, (alkyl) polyethylene glycols, (alkyl)polypropylene glycols or ethoxylated fatty alcohols, for example $C_{12}$–$C_{24}$-fatty alcohols reacted with 1 to 200 ethylene oxide units.

Also suitable are N,N-dialkylaminoalkyl acrylates and methacrylates and N-dialkylaminoalkylacryl- and -methacrylamides of the formula (VII)

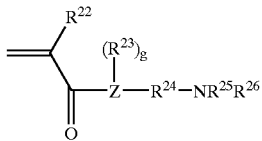

(VII)

where

R$^{22}$=H, alkyl having from 1 to 8 carbon atoms,

R$^{23}$=H, methyl,

R$^{24}$=alkylene having from 1 to 24 carbon atoms, optionally substituted by alkyl, R$^{25}$, R$^{26}$=C$_1$–C$_{40}$ alkyl radical, Z=nitrogen when g=1, or oxygen when g=0.

The amides can be unsubstituted, N-alkyl- or N-alkylamino-monosubstituted or N,N-dialkyl-substituted or N,N-dialkylamino-disubstituted, where the alkyl or alkylamino groups are derived from C$_1$–C$_{40}$ linear, C$_3$–C$_{40}$ branched, or C$_3$–C$_{40}$ carbocyclic units. In addition, the alkylamino groups can be quaternized.

Preferred comonomers of the formula VII are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N-[3-(dimethylamino)propyl]methacrylamide and N-[3-(dimethylamino)propyl]acrylamide.

Comonomers (b) which can likewise be used are substituted acrylic acids and salts, esters and amides thereof, where the substituents on the carbon atoms are in the two or three position of the acrylic acid, and are independently of one another chosen from the group consisting of C$_1$–C$_4$-alkyl, —CN, COOH, particularly preferably methacrylic acid, ethacrylic acid and 3-cyanoacrylic acid. These salts, esters and amides of these substituted acrylic acids can be chosen as described above for the salts, esters and amides of acrylic acid.

Other suitable comonomers (b) are allyl esters of C$_1$–C$_{40}$ linear, C$_3$–C$_{40}$ branched or C$_3$–C$_{40}$ carbocyclic carboxylic acids, vinyl or allyl halides, preferably vinyl chloride and allyl chloride, vinyl ethers, preferably methyl, ethyl, butyl or dodecyl vinyl ether, vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the formula VIII, in which R$^{27}$ to R$^{29}$, independently of one another, are hydrogen, C$_1$–C$_4$-alkyl or phenyl:

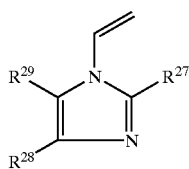

(VIII)

Further suitable comonomers (b) are diallylamines of the formula (IX)

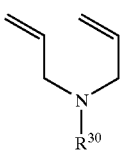

(IX)

where R$^{30}$=C$_1$–C$_{24}$-alkyl.

Further suitable comonomers (b) are vinylidene chloride; and hydrocarbons having at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable comonomers (b) are acrylic acid, methacrylic acid, ethylacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl (meth)acrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth)acrylates, unsaturated sulfonic acids such as, for example, acrylamidopropanesulfonic acid;

acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide;

maleic acid, fumaric acid, maleic anhydride and its monoesters, crotonic acid, itaconic acid, diallyldimethylammonium chloride, vinyl ethers (for example: methyl, ethyl, butyl or dodecyl vinyl ether), methyl vinyl ketone, maleimide, vinylpyridine, vinylimidazole, vinylfuran, styrene, styrene sulfonate, allyl alcohol, and mixtures thereof.

Of these, particular preference is given to acrylic acid, methacrylic acid, maleic acid, fumaric acid, crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids such as, for example, acrylamidopropanesulfonic acid, vinylpyrrolidone, vinylcaprolactam, vinyl ethers (e.g.: methyl, ethyl, butyl or dodecyl vinyl ether), 1-vinylimidazole, 1-vinyl-2-methylimidazole, N,N-dimethylaminomethyl methacrylate and N-[3-(dimethylamino)propyl]methacrylamide; 3-methyl-1-vinylimidazolium chloride, 3-methyl-1-vinylimidazolium methyl sulfate, N,N-dimethylaminoethyl methacrylate, N-[3-(dimethylamino)propyl]methacrylamide quaternized with methyl chloride, methyl sulfate or diethyl sulfate.

Monomers having one basic nitrogen atom can be quaternized in the following manner:

Suitable for quaternizing the amines are, for example, alkyl halides having 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Other suitable quaternizing agents are dialkyl sulfates, in particular dimethyl sulfate or diethyl sulfate. The quaternization of the basic amines can also be carried out with alkylene oxides such as ethylene oxide or propylene oxide in the presence of acids. Preferred quaternizing agents are: methyl chloride, dimethyl sulfate or diethyl sulfate.

The quaternization can be carried out before the polymerization or after the polymerization.

In addition, it is possible to use the reaction products of unsaturated acids, such as, for example, acrylic acid or methacrylic acid, with a quaternized epichlorohydrin of the formula (X) ($R^{31}$=$C_1$–$C_{40}$-alkyl).

(X)

Examples thereof are: (meth)acryloyloxyhydroxypropyltrimethylammonium chloride and (meth)acryloyloxyhydroxypropyltriethylammonium chloride.

The basic monomers can also be cationized, by neutralizing them with mineral acids, such as, for example, sulfuric acid, hydrochloric acid, hydrobromic acid, hydroiodic acid, phosphoric acid or nitric acid, or with organic acids, such as, for example, formic acid, acetic acid, lactic acid, or citric acid.

In addition to the abovementioned comonomers, it is possible to use, as comonomers (b), "macromonomers" such as, for example, silicone-containing macromonomers having one or more free-radically polymerizable groups or alkyloxazoline macromonomers, as described, for example, in EP 408 311.

Furthermore, it is possible to use monomers containing fluorine, as described, for example, in EP 558423, compounds which have a crosslinking action or compounds which regulate the molecular weight, in combination or alone.

Regulators which can be used are the customary compounds known to the person skilled in the art, such as, for example, sulfur compounds (e.g.: mercaptoethanol, 2-ethylhexyl thioglycolate, thioglycolic acid or dodecyl mercaptan), and tribromochloromethane and other compounds which have a regulating effect on the molecular weight of the resulting polymers.

In some instances, it is also possible to use silicone compounds which contain thiol groups.

Preference is given to using silicone-free regulators.

Crosslinking monomers which can be used are compounds having at least two ethylenically unsaturated double bonds, such as, for example, esters of ethylenically unsaturated carboxylic acids, such as acrylic acid or methacrylic acid and polyhydric alcohols, ethers of at least dihydric alcohols such as, for example, vinyl ethers or allyl ethers.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, neopentyl glycol hydroxypivalate, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1, 5-diol, and polyethylene glycols, polypropylene glycols and polytetrahydrofurans having molecular weights of in each case 200 to 10 000. Apart from the homopolymers of ethylene oxide and propylene oxide, it is also possible to use block copolymers of ethylene oxide or propylene oxide or copolymers which contain ethylene oxide and propylene oxide groups in incorporated form. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose. It is of course also possible to use the polyhydric alcohols following reaction with ethylene oxide or propylene oxide, as the corresponding ethoxylates or propoxylates respectively. The polyhydric alcohols can also firstly be converted into the corresponding glycidyl ethers by reaction with epichlorohydrin.

Further suitable crosslinkers are the vinyl esters or the esters of monohydric, unsaturated alcohols with ethylenically unsaturated $C_3$–$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example of oleic acid, crotonic acid, cinnamic acid or 10-undecenoic acid.

Also suitable are straight-chain or branched, linear or cyclic aliphatic or aromatic hydrocarbons which have at least two double bonds which, in the case of aliphatic hydrocarbons, must not be conjugated, e.g., divinylbenzene, divinyltoluene, 1,7-octadiene, 1,9-decadiene, 4-vinyl-1-cyclohexene, trivinylcyclohexane or polybutadienes having molecular weights of from 200 to 20 000.

Also suitable are amides of unsaturated carboxylic acids, such as, for example, acrylic acid and methacrylic acid, itaconic acid, maleic acid and N-allylamines of at least difunctional amines, such as, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides of allylamine and unsaturated carboxylic acids such as acrylic acid, methacrylic acid, itaconic acid, maleic acid, or at least dibasic carboxylic acids as have been described above.

Further suitable crosslinkers are triallylamine or corresponding ammonium salts, e.g. triallylmethylammonium chloride or triallylmethylammonium methyl sulfate.

It is also possible to use N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Further suitable crosslinkers are divinyldioxane, tetraallylsilane or tetravinylsilane.

Particularly preferred crosslinkers are, for example, methylenebisacrylamide, divinylbenzene, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and allyl or vinyl ethers of polyhydric alcohols, for example 1,2-ethanediol, 1,4-butanediol, diethylene glycol, trimethylolpropane, glycerol, pentaerythritol, sorbitan and sugars such as sucrose, glucose, mannose.

Very particularly preferred crosslinkers are pentaerythritol triallyl ethers, allyl ethers of sugars such as sucrose, glucose, mannose, divinylbenzene, methylenebisacrylamide, N,N'-divinylethyleneurea, and (meth)acrylic esters of glycol, butanediol, trimethylolpropane or glycerol or (meth)acrylic esters of glycol, butanediol, trimethylolpropane or glycerol reacted with ethylene oxide and/or epichlorohydrin.

The proportion of monomers which have a crosslinking action is 0 to 10% by weight, preferably 0 to 5% by weight, very particularly preferably 0 to 2% by weight.

In the polymerization for the preparation of the polymers according to the invention, in some instances other polymers, such as, for example, polyamides, polyurethanes, polyesters, homo- and copolymers of ethylenically unsaturated monomers, may also be present. Examples of such polymers, some of which are also used in cosmetics, are the polymers known under the trade names Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastma AQ™.

The comonomers (b) according to the invention can, provided they contain ionizable groups, be partially or completely neutralized with acids or bases before or after the polymerization in order, for example, to adjust the solubility or dispersibility in water to a desired degree.

Neutralizing agents for monomers carrying acid groups which can be used are, for example, mineral bases such as sodium carbonate, alkali metal hydroxides and ammonia, organic bases such as aminoalcohols, specifically 2-amino-2-methyl-1-propanol, monoethanolamine, diethanolamine, triethanolamine, triisopropanolamine, tri[(2-hydroxy)-1-propyl]amine, 2-amino-2-methyl-1,3-propanediol, 2-amino-2-hydroxymethyl-1,3-propanediol and diamines, such as, for example, lysine.

To prepare the polymers, the monomers of component a) and optionally of component B) may be polymerized in the presence of the graft base c) either using initiators which form free radicals, or by the action of high-energy radiation, which is also intended to mean the action of high-energy electrons.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butylperoxy-2-ethyl hexanoate, tert-butyl permaleate, cumene hydroperoxide, diisopropyl peroxydicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate.

Preference is given to using organic peroxides.

The polymerization can also be carried out by the action of ultraviolet radiation, optionally in the presence of UV initiators. For the polymerization under the action of UV rays, use is made of the suitable photoinitiators and/or or sensitizers customary for this purpose. These are, for example, compounds such as benzoin and benzoin ether, α-methylbenzoin or α-phenylbenzoin. It is also possible to use "triplet sensitizers", such as benzyl diketals. The UV radiation sources used are, for example, in addition to high-energy UV lamps, such as carbon arc lamps, mercury vapor lamps or xenon lamps, also low-UV light sources, such as fluorescent tubes with a high blue component.

The amounts of initiator or initiator mixtures used, based on monomer used, are between 0.01 and 10% by weight, preferably between 0.1 and 5% by weight.

The polymerization is carried out in the temperature range from 40 to 200° C., preferably in the range from 50 to 140° C., particularly preferably in the range from 60 to 110° C. It is usually carried out under atmospheric pressure, but can also be carried out under reduced or increased pressure, preferably between 1 and 5 bar.

The polymerization can, for example, be carried out as solution polymerization, bulk polymerization, emulsion polymerization, inverse emulsion polymerization, suspension polymerization, inverse suspension polymerization or precipitation polymerization, without the possible methods being limited thereto.

In the case of bulk polymerization, the procedure may involve dissolving the graft base c) in at least one monomer of group a) and possibly other comonomers of group b) and, after the addition of a polymerization initiator, fully polymerizing the mixture. The polymerization can also be carried out semicontinuously by firstly introducing some, e.g. 10%, of the mixture to be polymerized comprising the graft base c), at least one monomer of group a), possibly other comonomers of group b) and initiator, heating the mixture to the polymerization temperature and, after the polymerization has started, adding the remainder of the mixture to be polymerized in accordance with the progress of the polymerization. The polymers can also be obtained by initially introducing the graft base c) into a reactor, heating it to the olymerization temperature and adding at least one monomer of group a), possibly other comonomers of group b) and polymerization initiator either in one portion, step by step or, preferably, continuously, and polymerizing.

If desired, the above-described polymerization can also be carried out in a solvent. Suitable solvents are, for example, alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, glycerol and dioxane. The polymerization can also be carried out in water as solvent. In this case, the initial charge is a solution which, depending on the amount of monomers of component a) added, is soluble in water to a greater or lesser degree. In order to convert water-insoluble products, which can form during the polymerization, into solution, it is possible, for example, to add organic solvents, such as monohydric alcohols having from 1 to 3 carbon atoms, acetone or dimethylformamide. However, in the case of polymerization in water, it is also possible to convert the water-insoluble polymers into a finely divided dispersion by addition of customary emulsifiers or protective colloids, e.g. polyvinyl alcohol.

The emulsifiers used are, for example, ionic or nonionic surfactants whose HLB value is in the range from 3 to 13. The definition of the HLB value can be found in the publication by W. C. Griffin, J. Soc. Cosmetic Chem., Volume 5, 249 (1954).

The amount of surfactants, based on the polymer, is 0.1 to 10% by weight. Using water as solvent gives solutions or dispersions of the polymers. If solutions of the polymer are prepared in an organic solvent or in mixtures of an organic solvent and water, then, per 100 parts by weight of the polymer, 5 to 2 000, preferably 10 to 500, parts by weight of the organic solvent or of the solvent mixture are used.

Preference is given to polymers obtainable by free-radical graft copolymerization of
  a) 10–90% by weight of at least one open-chain N-vinylamide compound of the formula I and
  b) 0–60% by weight of one or more further copolymerizable monomers on
  c) 10–90% by weight of a water-soluble or water-dispersible polymeric graft base.

Particular preference is given to polymers obtainable by free-radical graft copolymerization of
  a) 20–80% by weight of at least one open-chain N-vinylamide compound of the formula I and
  b) 0–60% by weight of one or more further copolymerizable monomers on
  c) 20–80% by weight of one or more water-soluble or water-dispersible polymeric graft base.

Very particular preference is given to polymers obtainable by free-radical graft copolymerization of
  a) 40–80% by weight of at least one open-chain N-vinylamide compound of the formula I and
  b) 0–40% by weight of one or more further copolymerizable monomers on
  c) 20–80% by weight of one or more water-soluble or water-dispersible polymeric graft base.

The graft copolymers according to the invention can be saponified after the polymerization. The saponification produces a cationic group in the polymer. This may lead to increased solubility in water and improved conditioning properties in cosmetic applications.

From the above-described graft copolymers arise, by partial or complete elimination of the formyl groups or of the $C_1$–$C_6$-alkyl-C=O— groups from those open-chain N-vinylamides (IV) incorporated into the polymer, with the formation of amine and/or ammonium groups, units of the formula (V)

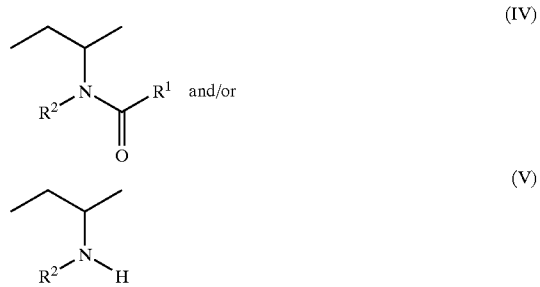

In the formulae (IV) and (V), the substituents $R^1$ and $R^2$ are each as defined above. Depending on the reaction conditions chosen during the hydrolysis, either partial or complete hydrolysis of the units (IV) is achieved.

If, in addition to the hydrolysis-insensitive vinylpyrrolidone units, the graft base also contains comonomers which are hydrolysis-sensitive, such as, for example, vinyl acetate or acrylamide, then hydrolysis also takes place in the graft base. Thus, vinyl acetate reacts to give vinyl alcohol groups, and acrylamide reacts to give acrylic acid groups.

Suitable hydrolysis agents are mineral acids, such as hydrogen halides, which can be used in gaseous form or in aqueous solution. Preference is given to using hydrochloric acid, sulfuric acid, nitric acid and phosphoric acid, and organic acids, such as $C_1$–$C_5$-carboxylic acids and aliphatic or aromatic sulfonic acids. 0.05 to 2 mol equivalents, preferably 1 to 1.5 mol equivalents, of an acid are required per formyl group equivalent which is to be eliminated from the copolymerized units (IV).

The hydrolysis of the copolymerized units of the structure (IV) can also be carried out using bases, e.g. metal hydroxides, in particular alkali metal and alkaline earth metal hydroxides. Preference is given to using sodium hydroxide or potassium hydroxide. The hydrolysis can optionally also be carried out in the presence of ammonia or amines.

The hydrolysis in the acidic or in the alkaline pH range takes place, for example, at temperatures of from 30 to 170, preferably 50 to 120° C. It is complete after about 2 to 8 hours, preferably 3 to 5 hours. After these reaction times, degrees of hydrolysis of the units of the copolymerized monomers of the formula (I) of from 1 to 100% are achieved. A particularly successful procedure has proven to be one in which the bases or acids are added in aqueous solution for the hydrolysis. After the hydrolysis, a neutralization is generally carried out, such that the pH of the hydrolyzed polymer solution is 2 to 8, preferably 3 to 7. Neutralization is required if a continuation of the hydrolysis of partially hydrolyzed polymers is to be avoided or delayed. The hydrolysis can also be carried out using enzymes.

The polymers prepared in this way can then be cationized by reaction of hydroxyl and/or amino functions present in the polymer with epoxides of the formula X ($R^{31}$=$C_1$ to $C_{40}$ alkyl).

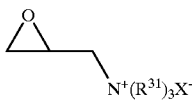
(X)

For this, the hydroxyl groups of the polyvinyl alcohol units and vinylamine units, formed by hydrolysis of vinylformamide, can preferably be reacted with the epoxides.

The epoxides of the formula X can also be produced in situ by reaction of the corresponding chlorohydrins with bases, for example sodium hydroxide.

Preference is given to using 2,3-epoxypropyltrimethylammonium chloride or 3-chloro-2-hydroxypropyltrimethylammonium chloride. The K values of the polymers should be in the range from 10 to 300, preferably 25 to 250, particularly preferably 25 to 200, very particularly preferably in the range from 30 to 150. The K value desired in each case can be adjusted in a manner known per se through the composition of the feed substances. The K values are determined in accordance with Fikentscher, Cellulosechemie, Vol. 13, pp. 58 to 64, and 71 to 74 (1932) in N-methylpyrrolidone at 25° C. and polymer concentrations which, depending on the K value range, are between 0.1% by weight and 5% by weight.

To remove solvents, the polymer solutions can be steam-distilled. Following steam distillation, aqueous solutions or dispersions are obtained depending on the choice of components a–c.

The polymers obtained can also be subsequently crosslinked by reacting the hydroxyl groups or amino groups in the polymer with at least bifunctional reagents. In the case of low degrees of crosslinking, water-soluble products are obtained, and in the case of high degrees of crosslinking, water-swellable or insoluble products are obtained.

For example, the polymers according to the invention can be reacted with dialdehydes and diketones, e.g. glyoxal, glutaraldehyde, succindialdehyde or terephthalaldehyde. Also suitable are aliphatic or aromatic carboxylic acids, for example maleic acid, oxalic acid, malonic acid, succinic acid or citric acid, or carboxylic acid derivatives, such as carboxylic esters, anhydrides or halides. Also suitable are polyfunctional epoxides, e.g. epichlorohydrin, glycidyl methacrylate, ethylene glycol diglycidyl ether, 1,4-butanediol diglycidyl ether or 1,4-bis(glycidyloxy)benzene. Also suitable are diisocyanates, for example hexamethylene diisocyanate, isophorone diisocyanate, methylenediphenyl diisocyanate, toluylene diisocyanate or divinylsulfone.

Also suitable are inorganic compounds, such as boric acid or boric acid salts, for example sodium metaborate, borax (disodium tetraborate), and salts of polyvalent cations, e.g. copper(II) salts, such as copper(II) acetate or zinc, aluminum, titanium salts.

Boric acid and/or boric acid salts, such as sodium metaborate or disodium tetraborate, are preferably suitable for the subsequent crosslinking. In this connection, boric acid and/or boric acid salts can, preferably as salt solutions, be added to the solutions of the polymers according to the invention. Preference is given to adding boric acid and/or boric acid salts to the aqueous polymer solutions.

The boric acid and/or boric acid salts can be added to the polymer solutions directly after preparation. It is, however, also possible to add the boric acid and/or boric acid salts subsequently to the cosmetic formulations containing the polymers according to the invention, or to add them during the preparation process of the cosmetic formulations.

The proportion of boric acid and/or boric acid salts, based on the polymers according to the invention, is 0 to 15% by weight, preferably 0 to 10% by weight, particularly preferably 0 to 5% by weight.

The polymer solutions and dispersions can be converted into powder form by a variety of drying methods, such as, for example, spray drying, fluidized spray drying, drum drying or freeze drying. The drying method used in preference is spray drying. The dry polymer powder obtained in this way can be used to prepare an aqueous solution or dispersion again, by dissolution or redispersion in water. Conversion into powder form has the advantage of better storability, easier transportation, and a lower propensity for microbial attack.

The water-soluble or water-dispersible graft copolymers according to the invention are highly suitable for use in cosmetic formulations.

The polymers according to the invention are suitable as styling agents and/or conditioning agents in hair cosmetic preparations, such as hair cures, hair lotions, hair rinses, hair emulsions, split-end fluids, neutralizers for permanent waves, "hot-oil treatment" preparations, conditioners, setting lotions or hairsprays. Depending on the field of application, the hair cosmetic preparations can be applied as spray, foam, gel, gel spray or mousse.

The hair cosmetic formulations according to the invention comprise, in a preferred embodiment, a) 0.05–20% by weight of the polymer according to the invention b) 20–99.95% by weight of water and/or alcohol c) 0–79.5% by weight of further constituents.

Alcohol is to be understood as meaning all alcohols customary in cosmetics, e.g. ethanol, isopropanol, n-propanol.

Further constituents are to be understood as meaning the additives customary in cosmetics, for example propellants, antifoams, interface-active compounds, i.e. surfactants, emulsifiers, foam formers and solubilizers. The interface-active compounds used can be anionic, cationic, amphoteric or neutral. Further customary constituents can also be, for example, preservatives, perfume oils, opacifiers, active ingredients, UV filters, care substances such as panthenol, collagen, vitamins, protein hydrolyzates, alpha- and beta-hydroxycarboxylic acids, stabilizers, pH regulators, colorants, viscosity regulators, gel formers, salts, moisturizers, refatting agents and further customary additives.

These also include all styling and conditioning polymers known in cosmetics which can be used in combination with the polymers according to the invention, in cases where very specific properties are to be set.

Suitable traditional hair cosmetic polymers are, for example, anionic polymers. Such anionic polymers are homo- and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes (Luviset® P.U.R.) and polyureas. Particularly suitable polymers are copolymers of t-butyl acrylate, ethyl acrylate, methacrylic acid (e.g. Luvimer® 100P), copolymers of N-tert-butylacrylamide, ethyl acrylate, acrylic acid (Ultrahold® 8, strong), copolymers of vinyl acetate, crotonic acid and optionally other vinyl esters (e.g. Luviset® grades), maleic anhydride copolymers, optionally reacted with alcohols, anionic polysiloxanes, e.g. carboxy-functional ones, copolymers of vinylpyrrolidone, t-butyl acrylate, methacrylic acid (e.g. Luviskol® VBM).

Very particularly preferred anionic polymers are acrylates with an acid number greater than or equal to 120 and copolymers of t-butyl acrylate, ethyl acrylate or methacrylic acid.

Other suitable hair cosmetic polymers are cationic polymers with the name polyquaternium according to INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam-N-vinylpyrrolidone/N-vinylimidazolium salts (Luviquat® Hold); cationic cellulose derivatives (polyquaternium-4 and -10), acrylamide copolymers (polyquaternium-7).

Other suitable hair cosmetic polymers are also neutral polymers such as polyvinylpyrrolidones, copolymers of N-vinylpyrrolidone and vinyl acetate and/or vinyl propionate, polysiloxanes, polyvinylcaprolactam and copolymers with N-vinylpyrrolidone, polyethyleneimines and salts thereof, polyvinylamines and salts thereof, cellulose derivatives, polyaspartic acid salts and derivatives.

To establish certain properties, the preparations can also additionally comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds such as amodimethicones (CTFA).

The polymers according to the invention are suitable in particular as setting agents in hairstyling preparations, in particular hairsprays (aerosol sprays and pump sprays without propellant gas) and hair foams (aerosol foams and pump foams without propellant gas).

In a preferred embodiment, these preparations comprise
 a) 0.1–10% by weight of the polymer according to the invention
 b) 20–99.9% by weight of water and/or alcohol
 c) 0–70% by weight of a propellant
 d) 0–20% by weight of further constituents.

Propellants are the propellants customarily used for hairsprays and aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises
 a) 0.1–10% by weight of the polymer according to the invention
 b) 55–94.8% by weight of water and/or alcohol
 c) 5–20% by weight of a propellant
 d) 0.1–5% by weight of an emulsifier
 e) 0–10% by weight of further constituents.

The emulsifiers which may be used are all emulsifiers customarily used in hair foams. Suitable emulsifiers may be nonionic, cationic or anionic.

Examples of nonionic emulsifiers (INCI nomenclature) are laureths, e.g. laureth-4; ceteths, e.g. ceteth-1, polyethylene glycol cetyl ether; cetearaths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methyl sulfate, quaternium-1 to x (INCI).

Anionic emulsifiers can, for example, be chosen from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have from 1 to 10 ethylene oxide or propylene oxide units, preferably 1 to 3 ethylene oxide units, in the molecule.

A preparation suitable according to the invention for styling gels may, for example, have the following composition:
 a) 0.1–10% by weight of the polymer according to the invention
 b) 60–99.85% by weight of water and/or alcohol
 c) 0.05–10% by weight of a gel former
 d) 0–20% by weight of further constituents.

The gel formers which can be used are all gel formers customary in cosmetics. These include slightly crosslinked polyacrylic acid, for example carbomer (INCI), cellulose derivatives, e.g. hydroxypropylcellulose, hydroxyethylcellulose, cationically modified celluloses, polysaccharides, e.g. xanthum gum, caprylic/capric triglycerides, sodium acrylates copolymer, polyquaternium-32 (and) paraffinum liquidum (INCI), sodium acrylates copolymer (and) paraffinum liquidum (and) PPG-1 trideceth-6, acrylamidopropyl trimonium chloride/acrylamide copolymer, steareth-10 allyl ether acrylates copolymer, polyquaternium-37 (and) paraffinum liquidum (and) PPG-1 trideceth-6, polyquaternium 37 (and) propylene glycol dicaprate dicaprylate (and) PPG-1 trideceth-6, polyquaternium-7, polyquaternium-44.

The polymers according to the invention can also be used in shampoo formulations as setting and/or conditioning agents. Polymers with a cationic charge are in particular suitable as conditioning agents.

Preferred shampoo formulations comprise
 a) 0.05–10% by weight of the polymer according to the invention
 b) 25–94.95% by weight of water
 c) 5–50% by weight of surfactants
 d) 0–5% by weight of a further conditioning agent
 e) 0–10% by weight of further cosmetic constituents.

In the shampoo formulations it is possible to use all anionic, neutral, amphoteric or cationic surfactants customarily used in shampoos.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium and ammonium and triethanolamine salts. The alkyl ether sulfates, alkyl ether phosphates and alkyl ether carboxylates can have from 1 to 10 ethylene oxide or propylene oxide units, preferably 1 to 3 ethylene oxide units, in the molecule.

Suitable examples are sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

It is possible, for example, to use cocodimethylsulfopropylbetaine, laurylbetaine, cocamidopropylbetaine or sodium cocamphopropionate.

Examples of suitable nonionic surfactants are the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkyl alkanolamides, fatty acid esters of polyethylene glycols, alkyl polyglycosides or sorbitan ether esters.

In addition, the shampoo formulations may comprise customary cationic surfactants, such as, for example, quaternary ammonium compounds, for example cetyltrimethylammonium chloride.

In the shampoo formulations it is possible to use customary conditioning agents in combination with the polymers according to the invention to achieve certain effects. These agents include, for example, cationic polymers with the INCI name polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). It is also possible to use protein hydrolyzates, and conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and amino-functional silicone compounds such as amodimethicones (CTFA).

SYNTHESIS EXAMPLES

Unless stated otherwise, the K values were determined using 1% strength aqueous solutions.

Example 1

72.8 g of polyethylene glycol having an average molecular weight of 4000 (Pluriol E 4000, BASF Aktiengesellschaft), 180 g of distilled water, 2.8 g of 75% strength phosphoric acid and 2.8 g of 50% strength sodium hydroxide solution are introduced into a stirred reactor with nitrogen inlet, reflux condenser and metering device, and are refluxed under nitrogen. Under reflux, 297.1 g of vinylformamide are metered in over 1.5 hours and 10 g of tert-butyl peroctoate in 32 g of triethylene glycol monomethyl ether are metered in over 2 hours, and the mixture is further polymerized to completion at this temperature for 1.5 hours. Since the reaction mixture becomes highly viscose over the course of the reaction, 250 g of distilled water are metered in 45 minutes after the start of polymerization over the course of 1.5 hours. When the reaction is complete, the mixture is diluted with 500 g of distilled water. The slightly yellowish polymer solution has a solids content of 36.3% and a K value of 47.4.

Example 2

Saponification of Example 1

500 g of the solution obtained in Example 1 are heated to 80° C. with 100 g of distilled water and 1 g of sodium pyrosulfite. After the addition of 33 g of 25% strength sodium hydroxide solution, the mixture is stirred for 3 hours at 80° C. After cooling, the mixture is adjusted to pH 8 using 15 g of 38% strength hydrochloric acid. The resulting solution is yellowish and slightly cloudy.

Example 3

163.8 g of polyethylene glycol having an average molecular weight of 9000 (Pluriol E 9000, BASF Aktiengesellschaft) are introduced into a stirred reactor with nitrogen inlet, reflux condenser and metering device, and melted under nitrogen. Over the course of one hour, 18.5 g of N-vinylformamide and 1.35 g of tert-butyl peroctoate in 16.1 g of triethylene glycol monomethyl ether are metered in over the course of 1.5 hours at 90° C. The mixture is then afterpolymerized for one hour. During the afterpolymerization, the reaction mixture is diluted with distilled water. The resulting polymer has a K value of 33.6.

Example 4

127.4 g of polyethylene glycol having an average molecular weight of 9000 (Pluriol E 9000, BASF Aktiengesellschaft) are melted in a stirred reactor with nitrogen inlet, reflux condenser and metering device. 54.6 g of N-vinylformamide and 70 mg of butanediol divinyl ether are metered in over the course of one hour, and 1.88 g of tert-butyl peroctoate in 16.1 g of triethylene glycol monomethyl ether are metered in over the course of 1.5 hours at 90° C., and then the mixture is afterpolymerized for one hour at this temperature. During the afterpolymerization, the mixture is diluted with distilled water. The K value of the slightly yellowish, clear solution is 41.2.

Example 5

72 g of PEG-PPG block copolymer having an average molecular weight of 8000 (Lutrol F 68, BASF Aktiengesellschaft), 180 g of distilled water, 2.8 g of 75% strength phosphoric acid and 2.8 g of 50% strength sodium hydroxide solution are introduced into a stirred reactor with nitrogen inlet, reflux condenser and metering device and heated to reflux under nitrogen. Under reflux, 410 g of vinylformamide are metered in over the course of 1.5 hours, and 10 g of tert-butyl peroctoate in 32 g of triethylene glycol monomethyl ether are metered in over 2 hours and the mixture is further polymerized to completion for 1.5 hours at this temperature. Since the reaction mixture becomes highly viscose in the course of the reaction, 250 g of distilled water are metered in 45 minutes after the start of polymerization over the course of 1.5 hours. When the reaction is complete, the mixture is diluted with 500 g of distilled water. The slightly yellowish polymer solution has a K value of 45.

Example 6

The polymerization is carried out analogously to Example 5 using 72 g of alkylpolyethylene glycol having an average molecular weight of 3500 (Pluriol A 2000, BASF Aktiengesellschaft). The resulting polymer solution has a K value of 48.

Example 7

The polymerization is carried out analogously to Example 5 using 103 g of polyethylene glycol having an average molecular weight of 20 000. The resulting polymer solution has a K value of 53.

Example 8

The polymerization is carried out analogously to Example 5 using 137 g of polyethylene glycol having an average molecular weight of 35 000. The resulting polymer solution has a K value of 57.

Example 9

The polymerization is carried out analogously to Example 5 using 103 g of polyethylene glycol having an average molecular weight of 20 000. The resulting polymer solution has a K value of 55.

Example 10

The polymerization is carried out analogously to Example 5 using 202 g of dimethicone copolyol (Belsil DMC 6031TM, Wacker Chemie GmbH). The resulting polymer solution has a K value of 47.

Example 11

The polymerization is carried out analogously to Example 5 using 137 g of ethoxylated polyethyleneimine (prepared from 12.5% of polyethyleneimine having an average molecular weight of 1400 and 87.5% of ethylene oxide). The resulting polymer solution has a K value of 49.

Example 12

1000 g of a 21.4% strength solution of polyvinylpyrrolidone having a K value of 85.0 are heated to 80° C. in a gentle stream of nitrogen in a stirred reactor with nitrogen inlet, reflux condenser and metering device. Over the course of two hours are then uniformly metered in 91.7 g of N-vinylformamide and within 2.5 hours 1.83 g of 2,2'-azobis (2-amidinopropane) dihydrochloride dissolved in 98.2 g of water. When the monomer feed is complete, the reaction mixture is diluted with 239 g of water. The mixture is then afterpolymerized for 30 minutes, the temperature is increased to 85° C. and, with the addition of 0.9 g of 2,2'-azobis(2-amidinopropane) dihydrochloride, the mixture is polymerized to completion for a further hour. The resulting polymer solution has a solids content of 22.5% and a K value of 85.1 (measured in 1% strength aqueous solution).

Example 13

1000 g of a 21.0% strength solution of polyvinylpyrrolidone having a K value of 90, 339 g of water and 0.9 g of sodium dihydrogenphosphate are heated to 80° C. in a gentle stream of nitrogen in a stirred reactor with nitrogen inlet, reflux condenser and metering device. Over the course of two hours are then uniformly metered in 90 g of N-vinylformamide and within 2.5 hours 1.8 g of 2,2'-azobis (2-amidinopropane) dihydrochloride dissolved in 98.2 g of water. When the monomer feed is complete, the reaction mixture is diluted with 300 g of water. The mixture is then afterpolymerized for 30 minutes, then the temperature is increased to 85° C. and, with the addition of 0.5 g of 2,2'-azobis(2-amidinopropane) dihydrochloride, the mixture is polymerized to completion for a further hour. The resulting polymer solution has a solids content of 16.1% and a K value of 87.6 (measured in 1% strength aqueous solution).

Example 14

428.6 g of a 21.0% strength solution of polyvinylpyrrolidone having a K value of 90, 690 g of water and 2.1 g of sodium dihydrogenphosphate are heated to 80° C. in a gentle stream of nitrogen in a stirred reactor with nitrogen inlet, reflux condenser and metering device. Over the course of two hours are then uniformly metered in 210 g of N-vinylformamide and within 2.5 hours 4.2 g of 2,2'-azobis (2-amidinopropane) dihydrochloride dissolved in 97.8 g of water. When the monomer feed is complete, the reaction mixture is diluted with 200 g of water. The mixture is then afterpolymerized for 30 minutes, then the temperature is increased to 85° C. and, with the addition of 0.8 g of 2,2'-azobis(2-amidinopropane) dihydrochloride, the mixture is polymerized to completion for a further hour. The resulting polymer solution has a solids content of 18.4% and a K value of 71.7 (measured in 1% strength aqueous solution).

Example 15

214 g of a 21.0% strength solution of polyvinylpyrrolidone having a K value of 90, 428 g of water and 19.3 g of N-vinylformamide are heated to 80° C. in a gentle stream of nitrogen in a stirred reactor with nitrogen inlet, reflux condenser and metering device. 0.39 g of 2,2'-azobis(2-amidinopropane) dihydrochloride is then added in one portion and polymerized for two hours at the reaction temperature. The temperature is then increased to 85° C. and, with the addition of 0.18 g of 2,2'-azobis(2-amidinopropane) dihydrochloride, the mixture is polymerized to completion for a further hour. The resulting polymer solution has a solids content of 9.7% and a K value of 85 (measured in 1% strength aqueous solution).

Example 16

231 g of a 30.3% strength solution of polyvinylpyrrolidone having a K value of 30, 405 g of water, 0.7 g of sodium dihydrogenphosphate and 30 g of N-vinylformamide are heated to 80° C. in a gentle stream of nitrogen in a stirred reactor with nitrogen inlet, reflux condenser and metering device. A vacuum is then applied to the reaction apparatus such that the mixture gently boils under reflux at the reaction temperature. 0.6 g of 2,2'-azobis(2-amidinopropane) dihydrochloride is then added in one portion and polymerized for two hours at the reaction temperature. The temperature is then increased to 85° C. and, with the addition of 0.3 g of 2,2'-azobis(2-amidinopropane) dihydrochloride, the mixture is polymerized to completion for a further hour. The resulting polymer solution has a solids content of 15.3% and a K value of 36.7 (measured in 1% strength aqueous solution).

Example 17

99 g of a 30.3% strength solution of polyvinylpyrrolidone having a K value of 30, 498 g of water, 0.7 g of sodium dihydrogenphosphate and 70 g of N-vinylformamide are heated to 90° C. in a gentle stream of nitrogen in a stirred reactor with nitrogen inlet, reflux condenser and metering device. 1.4 g of 2,2'-azobis(2-amidinopropane) dihydrochloride are then added in one portion and polymerized for two hours at the reaction temperature. The temperature is then increased to 95° C. and, with the addition of 0.7 g of 2,2'-azobis(2-amidinopropane) dihydrochloride, the mixture is polymerized to completion for a further hour. The resulting polymer solution has a solids content of 13.8% and a K value of 59.5 (measured in 1% strength aqueous solution).

Example 18

115.8 g of a 21.6% strength solution of polyvinylpyrrolidone having a K value of 90, 484 g of water, 0.3 g of sodium dihydrogenphosphate and 25 g of N-vinylformamide are heated to 70° C. in a gentle stream of nitrogen in a stirred reactor with nitrogen inlet, reflux condenser and metering device. A vacuum is then applied to the reaction apparatus such that the mixture gently boils under reflux at the reaction temperature. 0.5 g of 2,2'-azobis(2-amidinopropane) dihydrochloride is then added in one portion and polymerized for three hours at the reaction temperature. The vacuum is then lifted, the temperature is increased to 85° C. and, with the addition of a further 0.25 g of 2,2'-azobis(2-amidinopropane) dihydrochloride, the mixture is polymerized to completion for a further hour. The resulting polymer solution has a solids content of 7.6% and a K value of 74.9 (measured in 1% strength aqueous solution).

Example 19

116.8 g of a 21.4% strength solution of polyvinylpyrrolidone having a K value of 85, 483 g of water, 0.3 g of sodium dihydrogenphosphate and 25 g of N-vinylformamide are heated to 70° C. in a gentle stream of nitrogen in a stirred reactor with nitrogen inlet, reflux condenser and metering device. A vacuum is then applied to the reaction apparatus such that the mixture gently boils under reflux at the reaction temperature. 0.5 g of 2,2'-azobis(2-amidinopropane) dihydrochloride is then added in one portion and polymerized for three hours at the reaction temperature. The vacuum is then lifted, the temperature is increased to 85° C. and, with the addition of a further 0.25 g of 2,2'-azobis(2-amidinopropane) dihydrochloride, the mixture is polymerized to completion for a further hour. The resulting polymer solution has a solids content of 7.8% and a K value of 78 (measured in 1% strength aqueous solution).

Example 20

The polymerization is carried out analogously to Example 17 using a copolymer of 70% by weight vinylpyrrolidone and 30% by weight vinyl acetate having a K value of 30 (Luviskol VA 73, BASF Aktiengesellschaft) as graft base. The resulting polymer has a K value of 55.

Example 21

The polymerization is carried out analogously to Example 17 using a copolymer of 60% by weight vinylpyrrolidone and 40% by weight vinyl acetate having a K value of 30 (Luviskol VA 64, BASF Aktiengesellschaft) as graft base. The resulting polymer has a K value of 53.

Example 22

165 g of a 30.3% strength solution of polyvinylpyrrolidone having a K value of 30, 451.5 g of water, 0.5 g of sodium dihydrogenphosphate and 50 g of N-vinylformamide are heated to 90° C. in a gentle stream of nitrogen in a stirred reactor with nitrogen inlet, reflux condenser and metering device. 1.0 g of 2,2'-azobis(2-amidinopropane) dihydrochloride is then added in one portion and polymerized for two hours at the reaction temperature. The temperature is then increased to 95° C. and, with the addition of 0.5 g of 2,2'-azobis(2-amidinopropane) dihydrochloride, the mixture is polymerized to completion for a further hour. The resulting polymer solution has a solids content of 14.4% and a K value of 38.6 (measured in 1% strength aqueous solution).

Example 23
Saponification of Example 22

450 g of the polymer from Example 22 are heated to 80° C. Over the course of one hour, 52 g of 50% strength sodium hydroxide solution are added dropwise uniformly. The mixture is then stirred for two hours, cooled and adjusted to pH 7 with 62 g of concentrated hydrochloric acid. The degree of hydrolysis is 100%.

Example 24
Saponification of Example 22

450 g of the polymer from Example 22 are heated to 80° C. Over the course of one hour, 26 g of 50% strength sodium hydroxide solution are added dropwise uniformly. The mixture is then stirred for two hours, cooled and adjusted to pH 7 with 31 g of concentrated hydrochloric acid. The degree of hydrolysis is 50%.

Example 25

150 g of a 20% strength solution of partially saponified polyvinyl alcohol having an average molecular weight of 31 000 (Mowiol 4-88, Clariant), 498 g of water, 0.7 g of sodium dihydrogenphosphate and 70 g of N-vinylformamide are heated to 90° C. in a gentle stream of nitrogen in a stirred reactor with nitrogen inlet, reflux condenser and metering device. 1.4 g of 2,2'-azobis(2-amidinopropane) dihydrochloride are then added in one portion and polymerized for two hours at the reaction temperature. The temperature is then increased to 95° C. and, with the addition of 0.7 g of 2,2'-azobis(2-amidinopropane) dihydrochloride, the mixture is polymerized to completion for a further hour. The resulting polymer had a K value of 45.3 (measured in 1% strength aqueous solution).

Example 26

150 g of a 20% strength solution of partially saponified polyvinyl alcohol having an average molecular weight of 67 000 (Mowiol 8-88, Clariant), 498 g of water, 0.7 g of sodium dihydrogenphosphate and 70 g of N-vinylformamide are heated to 90° C. in a gentle stream of nitrogen in a stirred reactor with nitrogen inlet, reflux condenser and metering device. 1.4 g of 2,2'-azobis(2-amidinopropane) dihydrochloride are then added in one portion and polymerized for two hours at the reaction temperature. The temperature is then increased to 95° C. and, with the addition of 0.7 g of 2,2'-azobis(2-amidinopropane) dihydrochloride, the mixture is polymerized to completion for a further hour. The resulting polymer had a K value of 65.3 (measured in 1% strength aqueous solution).

Example 27

200 g of a 15% strength solution of completely saponified polyvinyl alcohol having an average molecular weight of 61 000 (Mowiol 10-98, Clariant), 498 g of water, 0.7 g of sodium dihydrogenphosphate and 70 g of N-vinylformamide are heated to 90° C. in a gentle stream of nitrogen in a stirred reactor with nitrogen inlet, reflux condenser and metering device. 1.4 g of 2,2'-azobis(2-amidinopropane) dihydrochloride are then added in one portion and polymerized for two hours at the reaction temperature. The temperature is then increased to 95° C. and, with the addition of 0.7 g of 2,2'-azobis(2-amidinopropane) dihydrochloride, the mixture is polymerized to completion for a further hour. The resulting polymer had a K value of 68.4 (measured in 1% strength aqueous solution).

Example 28
Saponification of Example 27

450 g of the polymer from Example 22 are heated to 80° C. Over the course of one hour, 52 g of 50% strength sodium hydroxide solution are added dropwise uniformly. The mixture is then stirred for two hours, cooled and adjusted to pH 7 with 62 g of concentrated hydrochloric acid. The degree of hydrolysis is 100%.

Example 29

1010 g of distilled water, 2.4 g of primary sodium phosphate and 97.1 g of potato starch (82.4% strength) are heated to 70° C. under a gentle stream of nitrogen in a stirred reactor with nitrogen inlet, reflux condenser and metering device. At this temperature, 120 g of N-vinylformamide are added over the course of 2 hours and 0.98 g of 2,2'-azobis(2-methylpropionamidine) dihydrochloride in 97.6 g of distilled water are added over 3 hours. The reaction solution is stirred for a further 3 hours at 70° C. The resulting white dispersion has a solids content of 15.0%.

Example 30

400 g of the dispersion from Example 24 (weight ratio of N-vinylformamide to potato starch=60:40) are added dropwise over the course of 5 minutes to the above-described reactor containing 53.0 g of 38% strength hydrochloric acid. The mixture is then heated to 70° C. for 8 hours. 90% strength hydrolysis of the polymer is achieved.

Example 31

1993 g of distilled water, 3.6 g of primary sodium phosphate and 40 g of maltodextrin are heated to 70° C. under a gentle stream of nitrogen in a stirred reactor with nitrogen inlet, reflux condenser and metering device. At this temperature, 160 g of N-vinylformamide are added over the course of 3 hours and 0.98 g of 2,2'-azobis(2-methylpropionamidine) dihydrochloride in 95 g of distilled water are added over 4 hours. The reaction solution is stirred for a further 2 hours at 70° C. The slightly cloudy solution has a solids content of 14.6% and a K value of 60.

Example 32

1996 g of distilled water, 1.4 g of primary sodium phosphate and 78.1 g of glycose syrup (76.8% strength) are heated to 70° C. under a gentle stream of nitrogen in a stirred reactor with nitrogen inlet, reflux condenser and metering device. At this temperature, 142 g of N-vinylformamide are added over the course of 2 hours and 0.7 g of 2,2'-azobis(2-methylpropionamidine) dihydrochloride in 95 g of distilled water are added over 3 hours. The reaction solution is stirred for a further 3 hours at 70° C. The clear, colorless viscose solution has a solids content of 15.7% and a K value of 71.1.

Example 33

| Feed 1: | vinylpyrrolidone | 140 g |
| | vinylformamide | 40 g |
| Feed 2: | ethanol | 60 g |
| Wako V 59 | 2,2'-azobis(2-methylbutyronitrile) | 0.5 g |
| Feed 3: | ethanol | 12 g |
| | Wako V 59 | 1.5 g |
| Initial charge: | ethanol | 30 g |
| | water, dist. | 120 g |
| | Mowiol 4/88 (20% strength) | 100 g |
| Feed 1 | | 18 g |
| Feed 2 | | 6 g |

100 g of a 20% strength solution of a partially saponified polyvinyl alcohol Mowiol 4 to 88 (Clariant), 18 g of Feed 1, 6 g of Feed 2 in 30 g of ethanol and 120 g of water are introduced into a stirred reactor with nitrogen inlet, reflux condenser and metering device and heated to about 80° C. in a gentle stream of nitrogen. The remaining Feed 1 is metered in over 3 h and Feed 2 is metered in over 4 h and the mixture is polymerized.

The polymer solution is maintained at 80° C. for a further 1 h with stirring. The Feed 3 is added over the course of about 30 min. at a temperature of about 80° C., and the product is further afterpolymerized for a further 3 h. The resulting polymer (referred to below as 33d) had a K value of 51.4 (measured in 1% strength N-methylpyrrolidone).

The following graft copolymers were prepared in accordance with this general procedure:

| Example No. | Vinyl-pyrrolidone (in % by weight) | Vinyl-formamide (in % by weight) | Polyvinyl alcohol (in % by weight) | K value (1% in NMP) |
|---|---|---|---|---|
| 33 a | — | 80 | 20 | undissolved, cannot be determined |
| 33 b | 50 | 30 | 20 | 58.9 |
| 33 c | 60 | 20 | 20 | 57.2 |
| 33 d | 70 | 20 | 10 | 51.4 |
| 33 e | 50 | 20 | 30 | 49.8 |

All products are preferably used as hair-setting polymers. They are very compatible with thickeners based on polyacrylic acid, e.g. Carbopol 940 (Goodrich) and good gels can be formulated using approximately 0.25 to 2% by weight Carbopol 940 in water.

Application Examples

Example 1

Aerosol Hair Foam Formulation:
  2.00% copolymer from Example 1
  2.00% Luviquat Mono LS (cocotrimonium methyl sulfate)
  67.7% water
  10.0% propane/butane 3.5 bar (20° C.)
  q.s. perfume oil

Example 2

Comparative Example
  2.00% polymer content Luviquat Hold (Polquaternium-46)
  2.00% Luviquat Mono LS (cocotrimonium methyl sulfate)
  67.7% water
  10.0% propane/butane 3.5 bar (20° C.)
  q.s. perfume oil

Example 3

Aerosol Hair Foam:

| | | INCI |
|---|---|---|
| 4.00% | copolymer from Example 17 | |
| 0.20% | Cremophor A 25 | Ceteareth-25 |
| 1.00% | Luviquat Mono CP | hydroxyethyl cetyldimonium phosphate |

-continued

| | INCI |
|---|---|
| 5.00% | ethanol |
| 1.00% | panthenol |
| 10.0% | propane/butane 3.5 bar (20° C.) |
| q.s. | perfume oil |
| ad 100% | water |

Example 4
Pump Foam:

| | | INCI |
|---|---|---|
| 2.00% | copolymer from Example 26 | |
| 2.00% | Luviflex Soft (polymer content) | |
| 1.20% | 2-amino-2-methyl-1-propanol | |
| 0.20% | Cremophor A 25 | |
| 0.10% | Uvinul P 25 | PEG-25 PABA |
| q.s. | preservative | |
| q.s. | perfume oil | |
| ad 100% | water | |

Example 5
Pump Spray:

| | | INCI |
|---|---|---|
| 4.00% | copolymer from Example 32 | |
| 1.00% | panthenol | |
| 0.10% | Uvinul MS 40 | Benzophenone-4 |
| q.s. | preservative | |
| q.s. | perfume oil | |
| ad 100% | water | |

Example 6
Pump Spray:

| | | INCI |
|---|---|---|
| 4.00% | copolymer from Example 22 | |
| 1.00% | panthenol | |
| 0.10% | Uvinul M 40 | Benzophenone-3 |
| q.s. | preservative | |
| q.s. | perfume oil | |
| ad 100% | ethanol | |

Example 7
Hairspray:

| | | INCI |
|---|---|---|
| 5.00% | copolymer from Example 10 | |
| 0.10% | silicone oil Dow Corning DC 190 | dimethicone copolyol |
| 35.00% | dimethyl ether | |
| 5.00% | n-pentane | |
| ad 100% | ethanol | |
| q.s. | perfume oil | |

Example 8
Hairspray VOC 55%:

| | | INCI |
|---|---|---|
| 3.00% | copolymer from Example 4 | |
| 7.00% | Luviset P.U.R. | Polyurethane-1 |
| 40.00% | dimethyl ether | |
| 15.00% | ethanol | |
| q.s. | perfume oil | |
| ad 100% | water | |

Example 9
Hair Gel:

| | | INCI |
|---|---|---|
| 0.50% | Carbopol 980 | Carbomer |
| 3.00% | copolymer from Example 33b | |
| 0.10% | phytantriol | |
| 0.50% | panthenol | |
| q.s. | perfume oil | |
| q.s. | preservative | |
| ad 100% | water | |

Example 10
Hair Shampoo and Shower Gel

| | | INCI |
|---|---|---|
| 0.50% | copolymer from Example 27 | |
| 40.00% | Texapon NSO | Sodium Laureth Sulfate |
| 5.00% | Tego Betaine L 7 | Cocamidopropyl Betaine |
| 5.00% | Plantacare 2000 | Decyl Glucoside |
| 1.00% | propylene glycol | |
| q.s. | citric acid | |
| q.s. | preservative | |
| 1.00% | sodium chloride | |
| ad 100% | water | |

Application Example 11
Skin Cream

A water/oil cream emulsion (skin cream A) according to the invention was firstly prepared in accordance with the following formulation:

| | Additive | % by wt. |
|---|---|---|
| Cremophor A 6 | Ceteareth-6 and stearyl alcohol | 2.0 |
| Cremophor A 25 | Ceteareth-25 | 2.0 |
| Lanette O | Cetearyl alcohol | 2.0 |
| Imwitor 960 K | Glyceryl stearate SE | 3.0 |
| Paraffin oil | | 5.0 |
| Jojoba oil | | 4.0 |
| Luvitol EHO | Cetearyl octanoate | 3.0 |
| ABIL 350 | Dimethicone | 1.0 |
| Amerchol L 101 | Mineral oil and lanolin alcohol | 3.0 |
| Veegum Ultra | Magnesium aluminum silicate | 0.5 |
| 1,2-propylene glycol | Propylene glycol | 5.0 |
| Abiol | Imidazolidinylurea | 0.3 |
| Phenoxyethanol | | 0.5 |
| D-Panthenol USP | | 1.0 |
| Polymer (Preparation Example 28) | | 0.5 |
| Water | | ad 100 |

Two comparison creams were prepared in the same way:
Skin cream B (without the addition of polymer)

The following comparison tests 1 and 2 were carried out with these skin creams A and B to assess the feel on the skin.

100 µl of the emulsion were distributed uniformly on the backs of the hands, and the feel on the skin was tested subjectively after a contact time of 30 minutes. In each case, two emulsions (right/left hand) were compared with one another. The test was carried out by 10 subjects in each case.

Grade Scale:

2 (significantly softer than comparison cream)

1 (somewhat softer than comparison cream)

0 (identical)

−1 (somewhat rougher than comparison cream)

−2 (significantly rougher than comparison cream)

Result of comparison test 1 (comparison of skin cream A and comparison cream B):

| Grade | Number of subjects |
|---|---|
| 2 | 5 |
| 1 | 4 |
| 0 | 1 |
| −1 | — |
| −2 | — |

Application Example 12

Shower Gel

A shower gel formulation (shower gel A) of the invention was firstly prepared according to the following formulation:

| | Additive | % by wt. |
|---|---|---|
| Texapon NSO | Sodium laureth sulfate | 40.0 |
| Tego Betaine L7 | Cocamidopropylbetaine | 5.0 |
| Plantacare 2000 | Decyl glucoside | 5.0 |
| Perfume | | 0.2 |
| Polymer according to Preparation Example 30 | | 0.2 |
| Euxyl K 100 | Benzyl alcohol, methylchloro-isothiazolinone, methylisothiazolinone | 0.1 |
| D-Panthenol USP | | 0.5 |
| Citric acid (pH 6–7) | | q.s. |
| NaCl | | 2.0 |
| Water | | ad 100 |

Three comparison shower gels were prepared in the same way:

Shower gel B: (copolymer according to the invention replaced by the same amount of cationically modified hydroxyethylcellulose)

Shower gel C: (without the addition of polymer)

The following comparison test 3 was carried out with shower gels A, B and C to determine the creaminess of the lather:

2.0 g of each of the abovementioned formulations were applied to the palm of the left hand, lathered with tap water and, after rubbing for 1 minute between both hands, the feel of the lather in the palms of the hands was assessed:

Grade 1: very creamy

Grade 2: creamy

Grade 3: flat/lacking substance

Result of comparison test 3 (average grading from 10 subjects):

| Shower gel | Average from 10 subjects |
|---|---|
| A | 1.3 |
| B | 2.1 |
| C | 2.8 |

Application Example 13

Humectant Formulation

Formulation A

| | | Additive | % by wt. |
|---|---|---|---|
| a) | Cremophor A6 | Ceteareth-6 and stearyl alcohol | 2.0 |
| | Cremophor A25 | Ceteareth-25 | 2.0 |
| | Paraffin oil (high-viscosity) | | 10 |
| | Lanette O | Cetearyl alcohol | 2.0 |
| | Stearic acid | | 3.0 |
| | Nip-Nip | Methylparaben/propylparaben 70:30 | 0.5 |
| | Abiol | Imidazolidinylurea | 0.5 |
| b) | Polymer (Preparation Example 3) | | 3.0 |
| | Water | | ad 100.0 |

The two phases were heated to 80° C., phase a) was stirred into b), homogenized and stirred until cold, and then the mixture was adjusted to pH 6 with 10% strength aqueous NaOH solution.

A comparison cream (formulation B) was prepared in the same way without the addition of polymer.

A subject test on 8 subjects was carried out with formulations A and B. For this, the formulations were in each case applied to the forearm of the subjects in an amount of 2 mg/cm$^2$. After 30 min, the moisture content of the skin was determined using a Corneometer CM 825 (Khazaka & Courage). Following the application of formulation A, an average value of 45 corneometer units was measured, and with formulation B an average value of 35 was measured.

Application Example 14

O/W Cream for Retaining Skin Moisture

| Additive | % by wt. |
|---|---|
| Glycerol monostearate | 2.0 |
| Cetyl alcohol | 3.0 |
| Paraffin oil, subliquidum | 15.0 |
| Vaseline | 3.0 |
| Caprylic/capric triglyceride | 4.0 |
| Octyldodecanol | 2.0 |
| Hydrogenated coconut fat | 2.0 |
| Cetyl phosphate | 0.4 |
| Polymer (Preparation Example 33) | 3.0 |
| Glycerol | 3.0 |
| Sodium hydroxide | q.s. |
| Perfume oil | q.s. |
| Preservative | q.s. |
| Water | ad 100 |

Application Example 15
O/W Lotion

| Additive | % by wt. |
| --- | --- |
| Stearic acid | 1.5 |
| Sorbitan monostearate | 1.0 |
| Sorbitan monooleate | 1.0 |
| Paraffin oil, subliquidum | 7.0 |
| Cetyl alcohol | 1.0 |
| Polydimethylsiloxane | 1.5 |
| Glycerol | 3.0 |
| Polymer (Preparation Example 30) | 0.5 |
| Perfume oil | q.s. |
| Preservative | q.s. |
| Water | ad 100 |

Application Example 16
W/O Cream

| Additive | % by wt. |
| --- | --- |
| PEG-7 hydrogenated castor oil | 4.0 |
| Wool wax alcohol | 1.5 |
| Beeswax | 3.0 |
| Triglyceride, liquid | 5.0 |
| Vaseline | 9.0 |
| Ozokerite | 4.0 |
| Paraffin oil, subliquidum | 4.0 |
| Glycerol | 2.0 |
| Polymer (Preparation Example 29) | 2.0 |
| Magnesium sulfate*7$H_2$O | 0.7 |
| Perfume oil | q.s. |
| Preservative | q.s. |
| Water | ad 100 |

Application Example 17
Skincare Hydrogel

| Additive | % by wt. |
| --- | --- |
| Polymer (Preparation Example 10) | 3.0 |
| Sorbitol | 2.0 |
| Glycerol | 3.0 |
| Polyethylene glycol 400 | 5.0 |
| Ethanol | 1.0 |
| Perfume oil | q.s. |
| Preservative | q.s. |
| Water | ad 100 |

Application Example 18
Hydrodispersion Gel

| Additive | % by wt. |
| --- | --- |
| Polymer (Preparation Example 26) | 3.0 |
| Sorbitol | 2.0 |
| Glycerol | 3.0 |
| Polyethylene glycol 400 | 5.0 |
| Triglyceride, liquid | 2.0 |
| Ethanol | 1.0 |
| Perfume oil | q.s. |
| Preservative | q.s. |
| Water | ad 100 |

Application Example 19
Liquid Soap

| Additive | % by wt. |
| --- | --- |
| Coconut fatty acid, potassium salt | 15 |
| Potassium oleate | 3 |
| Glycerol | 5 |
| Polymer (Preparation Example 28) | 2 |
| Glycerol stearate | 1 |
| Ethylene glycol distearate | 2 |
| Specific additives, complexing agents, fragrances | q.s. |
| Water | ad 100 |

Application Example 20
Bodycare Cream

| Additive | | % by wt. |
| --- | --- | --- |
| Cremophor A6 | Ceteareth-6 and stearyl alcohol | 2.0 |
| Cremophor A 25 | Ceteareth-25 | 2.0 |
| Grape (Vitis vinifera) | seed oil | 6.0 |
| Glyceryl stearate SE | | 3.0 |
| Cetearyl alcohol | | 2.0 |
| Dimethicone | | 0.5 |
| Luvitol EHO | Cetearyl octanoate | 8.0 |
| Oxynex 2004 | Propylene glycol, BHT, ascorbyl palmitate, glyceryl stearate, citric acid | 0.1 |
| Preservative | | q.s. |
| 1,2-Propylene glycol USP | | 3.0 |
| Glycerol | | 2.0 |
| EDTA BD | | 0.1 |
| D-Panthenol USP | | 1.0 |
| Water | | ad 100 |
| Polymer (Preparation Example 7) | | 1.5 |
| Tocopheryl acetate | | 0.5 |

The formulation had a pH of 6.8. The viscosity (Brookfield [lacuna]

In the application examples below, all the amounts are in % by weight.

Application Example 21
Liquid Make-Up

A 1.70 glyceryl stearate 1.70 cetyl alcohol 1.70 ceteareth-6

1.70 ceteareth-25

5.20 caprylic/capric triglyceride 5.20 mineral oil

B q.s. preservative 4.30 propylene glycol 2.50 polymer according to Preparation Example 11

59.50 dist. water

C
q.s. perfume oil
D
2.00 iron oxides
12.00 titanium dioxide
Preparation:
Heat phase A and phase B separately to 80° C. Then mix phase B into phase A using a stirrer. Cool to 40° C. and add phase C and phase D. Homogenize repeatedly.

Application Example 22
Oil-Free Make-Up
A
0.35 veegum
5.00 butylene glycol
0.15 xanthan gum
B
53.0 dist. water
q.s. preservative
0.2 polysorbate-20
1.6 tetrahydroxypropylethylenediamine
C
1.0 silica
2.0 nylon-12
4.15 mica
6.0 titanium dioxide
1.85 iron oxides
D
4.0 stearic acid
1.5 glyceryl stearate
7.0 benzyl laurate
5.0 isoeicosane
q.s. preservative
E
1.0 dist. water
0.5 panthenol
0.1 imidazolidinylurea
5.0 polymer according to Preparation Example 6
Preparation:
Wet phase A with butylene glycol, add to phase B and mix thoroughly. Heat phase AB to 75° C. Pulverize phase C feed substances, add to phase AB and homogenize thoroughly. Mix feed substances of phase D, heat to 80° C. and add to phase ABC. Mix for some time until the mixture is homogeneous. Transfer the mixture to a vessel fitted with a propeller mixer. Mix feed substances of phase E, add to phase ABCD and mix thoroughly.

Application Example 23
Eyeliner
A
40.6 dist. water
0.2 disodium EDTA
q.s. preservative
B
0.6 xanthan gum
0.4 veegum
3.0 butylene glycol
0.2 polysorbate-20
C
15.0 iron oxide/Al powder/silica (e.g. Sicopearl Fantastico Gold™ from BASF)
D
10.0 dist. water
30.0 polymer according to Preparation Example 9
Preparation:
Premix phase B. Mix phase B into phase A using a propeller mixer, allowing the thickener to swell. Wet phase C with phase D, add the mixture to phase AB and mix thoroughly.

Application Example 24
Shimmering Gel
A
32.6 dist. water
0.1 disodium EDTA
25.0 carbomer (2% strength aqueous solution)
0.3 preservative
B
0.5 dist. water
0.5 triethanolamine
C
10.0 dist. water
9.0 polymer according to Preparation Example 31
1.0 polyquaternium-46
5.0 iron oxide
D
15.0 dist. water
1.0 D-panthenol 50 P (panthenol and propylene glycol)
Preparation:
Thoroughly mix the feed substances of phase A in the order given using a propeller mixer. Then add phase B to phase A. Stir slowly until the mixture is homogeneous. Thoroughly homogenize phase C until the pigments are well distributed. Add phase C and phase D to phase AB and mix thoroughly.

Application Example 25
Waterproof Mascara
A
46.7 dist. water
3.0 Lutrol E 400 (PEG-8)
0.5 xanthan gum
q.s. preservative
0.1 imidazolidinylurea
1.3 tetrahydroxypropylethylenediamine
B
8.0 carnauba wax
4.0 beeswax
4.0 isoeicosane
4.0 polyisobutene
5.0 stearic acid
1.0 glyceryl stearate
q.s. preservative
2.0 benzyl laurate
C
10.0 iron oxide/Al powder/silica (e.g. Sicopearl Fantastico Gold™ from BASF)
E
8.0 polyurethane-1
2.0 polymer according to Preparation Example 38

Preparation:

Heat phase A and phase B separately to 85° C. Maintain the temperature and add phase C to phase A and homogenize until the pigments are uniformly distributed. Add phase B to phase AC and homogenize for 2–3 minutes. Then add phase E and stir slowly. Cool the mixture to room temperature.

Application Example 26
Sun Protection Gel
Phase A
1.00 PEG-40 hydrogenated castor oil
8.00 octyl methoxycinnamate (Uvinul MC 80™ from BASF)
5.00 octocrylene (Uvinul N 539™ from BASF)
0.80 octyl triazone (Uvinul T 150™ from BASF)
2.00 butyl methoxydibenzoylmethane (Uvinul BMBM™ from BASF)
2.00 tocopheryl acetate
q.s. perfume oil
Phase B
2.50 polymer according to Preparation Example 26
0.30 acrylates/C10–30 alkyl acrylate crosspolymer
0.20 carbomer
5.00 glycerol
0.20 disodium EDTA
q.s. preservative
72.80 dist. water
Phase C
0.20 sodium hydroxide
Preparation:

Mix the components of phase A. Allow phase B to swell and stir into phase A with homogenization. Neutralize with phase C and homogenize again.

Application Example 27
Sun Protection Emulsion Containing $TiO_2$ and $ZnO_2$
Phase A
6.00 PEG-7 hydrogenated castor oil
2.00 PEG-45/dodecyl glycol copolymer
3.00 isopropyl myristate
8.00 jojoba (Buxus chinensis) oil
4.00 octyl methoxycinnamate (Uvinul MC 80)
2.00 4-methylbenzylidene camphor (Uvinul MBC 95)
3.00 titanium dioxide, dimethicone
1.00 dimethicone
5.00 zinc oxide, dimethicone
Phase B
2.00 polymer according to Preparation Example 24
0.20 disodium EDTA
5.00 glycerol
q.s. preservative
58.80 dist. water
Phase C
q.s. perfume oil
Preparation:

Heat phases A and B separately to about 85° C. Stir phase B into phase A and homogenize. Cool to about 40° C., add phase C and briefly homogenize again.

Application Example 28
Sun Protection Lotion
Phase A
6.00 octyl methoxycinnamate (Uvinul MC80™ from BASF)
2.50 4-methylbenzylidene camphor (Uvinul MBC 95™ from BASF)
1.00 octyl triazone (Uvinul T 150™ from BASF)
2.00 butyl methoxydibenzoylmethane (Uvinul BMBM™ from BASF)
2.00 PVP/hexadecene copolymer
5.00 PPG-3 myristyl ether
0.50 dimethicone
0.10 BHT, ascorbyl palmitate, citric acid, glyceryl stearate, propylene glycol
2.00 cetyl alcohol
2.00 potassium cetyl phosphate
Phase B
2.50 polymer according to Preparation Example 25
5.00 propylene glycol
0.20 disodium EDTA
q.s. preservative
63.92 dist. water
Phase C
5.00 mineral oil
0.20 carbomer
Phase D
0.08 sodium hydroxide
Phase E
q.s. perfume oil
Preparation:

Heat phases A and B separately to about 80° C. Stir phase B into phase A with homogenization, briefly afterhomogenize. Slurry phase C, stir into phase AB, neutralize with phase D and afterhomogenize. Cool to about 40° C., add phase E, homogenize again.

Application Example 29
Removable Face Mask
Phase A
57.10 dist. water
6.00 polyvinyl alcohol
5.00 propylene glycol
Phase B
20.00 alcohol
4.00 PEG-32
q.s. perfume oil
Phase C
5.00 polyquaternium-44
2.70 polymer according to Preparation Example 8
0.20 allantoin
Preparation Heat phase A to at least 90° C. and stir until dissolved. Dissolve phase B at 50° C. and stir into phase A. At about 35° C. compensate the ethanol loss. Add phase C and stir.

Application Example 30
Face Mask
Phase A
3.00 ceteareth-6
1.50 ceteareth-25
5.00 cetearyl alcohol
6.00 cetearyl octanoate 6.00 mineral oil
0.20 bisabolol
3.00 glyceryl stearate
Phase B
2.00 propylene glycol
5.00 panthenol
2.80 polymer according to Preparation Example 7
q.s. preservative
65.00 dist. water
Phase C
q.s. perfume oil
0.50 tocopheryl acetate
Preparation;
Heat phase A and B separately to about 80° C. Stir phase B into phase A with homogenization, briefly afterhomogenize. Cool to about 40° C., add phase C, homogenize again.

Application Example 31
Body Lotion Foam
Phase A
1.50 ceteareth-25
1.50 ceteareth-6
4.00 cetearyl alcohol
10.00 cetearyl octanoate
1.00 dimethicone
Phase B
3.00 polymer according to Preparation Example 2
2.00 panthenol
2.50 propylene glycol
q.s. preservative
74.50 dist. water
Phase C
q.s. perfume oil
Preparation:
Heat phases A and B separately to about 80° C. Stir phase B into phase A and homogenize. Cool to about 40° C., add phase C and briefly homogenize again. Containerizing: 90% of active ingredient and 10% propane/butane at 3.5 bar (20° C.).

Application Example 32
Face Wash for Dry and Sensitive Skin
Phase A
2.50 PEG-40 hydrogenated castor oil
q.s. perfume oil
0.40 bisabolol
Phase B
3.00 glycerol
1.00 hydroxyethyl cetyldimonium phosphate
5.00 witch hazel (Hamamelis Virginiana) distillate
0.50 panthenol
0.50 polymer according to Preparation Example 25
q.s. preservative
87.60 dist. water
Preparation:
Dissolve phase A until clear. Stir phase B into phase A.

Application Example 33
Face Wash Paste with Peeling Effect
Phase A
70.00 dist. water
3.00 polymer according to Preparation Example 15
1.50 carbomer
q.s. preservative
Phase B
q.s. perfume oil
7.00 potassium cocoyl hydrolyzed protein
4.00 cocamidopropylbetaine
Phase C
1.50 triethanolamine
Phase D
13.00 polyethylene (Luwax A™ from BASF)
Preparation:
Allow phase A to swell. Dissolve phase B until clear. Stir phase B into phase A. Neutralize with phase C. Then stir in phase D.

Application Example 34
Face soap
Phase A
25.0 potassium cocoate
20.0 disodium cocoamphodiacetate
2.0 lauramide DEA
1.0 glycol stearate
2.0 polymer according to Preparation Example 23
50.0 dist. water
q.s. citric acid
Phase B
q.s. preservative
q.s. perfume oil
Preparation:
Heat phase A to 70° C. with stirring until homogeneous. Adjust pH to 7.0 to 7.5 with citric acid. Cool to 50° C. and add phase B.

Application Example 35
Face cleansing Milk, O/W Type
Phase A
1.50 ceteareth-6
1.50 ceteareth-25
2.00 glyceryl stearate
2.00 cetyl alcohol
10.00 mineral oil
Phase B
5.00 propylene glycol
q.s. preservative
1.0 polymer according to Preparation Example 29
66.30 dist. water
Phase C
0.20 carbomer
10.00 cetearyl octanoate
Phase D
0.40 tetrahydroxypropylethylenediamine
Phase E
q.s. perfume oil
0.10 bisabolol
Preparation:
Heat phases A and B separately to about 80° C. Stir phase B into phase A with homogenization, and briefly afterhomogenize. Slurry phase C, stir into phase AB, neutralize with phase D and afterhomogenize. Cool to about 40° C., add phase E, homogenize again.

Application Example 36
Transparent Soap
 4.20 sodium hydroxide
 3.60 dist. water
 2.0 polymer according to Preparation Example 32
 22.60 propylene glycol
 18.70 glycerol
 5.20 cocoamide DEA
 10.40 cocamine oxide
 4.20 sodium lauryl sulfate
 7.30 myristic acid
 16.60 stearic acid
 5.20 tocopherol
Preparation:
 Mix all ingredients. Melt the mixture at 85° C. until clear. Immediately pour into the mold.

Application Example 37
Peeling Cream, O/W Type
 Phase A
 3.00 ceteareth-6
 1.50 ceteareth-25
 3.00 glyceryl stearate
 5.00 cetearyl alcohol, sodium cetearyl sulfate
 6.00 cetearyl octanoate
 6.00 mineral oil
 0.20 bisabolol
 Phase B
 2.00 propylene glycol
 0.10 disodium EDTA
 3.00 polymer according to Preparation Example 33e
 q.s. preservative
 59.70 dist. water
 Phase C
 0.50 tocopheryl acetate
 q.s. perfume oil
 Phase D
 10.00 polyethylene
Preparation:
 Heat phases A and B separately to about 80° C. Stir phase B into phase A and homogenize. Cool to about 40° C., add phase C and briefly homogenize again. Then stir in phase D.

Application Example 38
Shaving Foam
 6.00 ceteareth-25
 5.00 poloxamer 407
 52.00 dist. water
 1.00 triethanolamine
 5.00 propylene glycol
 1.00 PEG-75 lanolin oil
 5.00 polymer according to Preparation Example 5
 q.s. preservative
 q.s. perfume oil
 25.00 sodium laureth sulfate
Preparation:
 Weigh everything together, then stir until dissolved. Containerizing: 90 parts of active substance and 10 parts of 25:75 propane/butane mixture.

Application Example 39
Aftershave Balsam
 Phase A
 0.25 acrylates/C10–30 alkyl acrylate crosspolymer
 1.50 tocopheryl acetate
 0.20 bisabolol
 10.00 caprylic/capric triglyceride
 q.s. perfume oil
 1.00 PEG-40 hydrogenated castor oil
 Phase B
 1.00 panthenol
 15.00 alcohol
 5.00 glycerol
 0.05 hydroxyethylcellulose
 1.92 polymer according to Preparation Example 2
 64.00 dist. water
 Phase C
 0.08 sodium hydroxide
Preparation:
 Mix the components of phase A. Stir phase B into phase A with homogenization, then briefly afterhomogenize. Neutralize with phase C and homogenize again.

Application Example 40
Bodycare Cream
 Phase A
 2.00 ceteareth-6
 2.00 ceteareth-25
 2.00 cetearyl alcohol
 3.00 glyceryl stearate SE
 5.00 mineral oil
 4.00 jojoba (Buxus Chinensis) oil
 3.00 cetearyl octanoate
 1.00 dimethicone
 3.00 mineral oil, lanolin alcohol
 Phase B
 5.00 propylene glycol
 0.50 veegum
 1.00 panthenol
 1.70 polymer according to Preparation Example 4
 6.00 polyquaternium-44
 q.s. preservative
 60.80 dist. water
 Phase C
 q.s. perfume oil
Preparation:
 Heat phases A and B separately to about 80° C. Homogenize phase B. Stir phase B into phase A with homogenization, then briefly afterhomogenize.
 Cool to about 40° C., add phase C and briefly homogenize again.

Application Example 41
Toothpaste
 Phase A
 34.79 dist. water 3.00 polymer according to Preparation Example 31
0.30 preservative
20.00 glycerol
0.76 sodium monofluorophosphate
Phase B
1.20 sodium carboxymethylcellulose
Phase C
0.80 aroma oil
0.06 saccharin
0.10 preservative
0.05 bisabolol
1.00 panthenol
0.50 tocopheryl acetate
2.80 silica
1.00 sodium lauryl sulfate
7.90 dicalcium phosphate anhydrate
25.29 dicalcium phosphate dihydrate
0.45 titanium dioxide Preparation:
Dissolve phase A. Spread phase B into phase A and dissolve. Add phase C and stir under reduced pressure at RT for about 45 min.

Application Example 42
Mouthwash
Phase A
2.00 aroma oil
4.00 PEG-40 hydrogenated castor oil
1.00 bisabolol
30.00 alcohol
Phase B
0.20 saccharin
5.00 glycerol
q.s. preservative
5.00 poloxamer 407
0.5 polymer according to Preparation Example 7
52.30 dist. water Preparation:
Dissolve phase A and phase B separately until clear. Stir phase B into phase A.

Application Example 43
Denture Adhesive
Phase A
0.20 bisabolol
1.00 beta-carotene
q.s. aroma oil
20.00 cetearyl octanoate
5.00 silica
33.80 mineral oil
Phase B
5.00 polymer according to Preparation Example 15
35.00 PVP (20% strength solution in water)

Preparation:
Thoroughly mix phase A. Stir phase B into phase A.

Application Example 32
Skincare Cream, O/W Type
Phase A
8.00 cetearyl alcohol
2.00 ceteareth-6
2.00 ceteareth-25
10.00 mineral oil
5.00 cetearyl octanoate
5.00 dimethicone
Phase B
3.00 polymer according to Preparation Example 19
2.00 panthenol, propylene glycol
q.s. preservative
63.00 dist. water
Phase C
q.s. perfume oil Preparation:
Heat phase A and B separately to about 80° C. Stir phase B into phase A with homogenization, then briefly afterhomogenize. Cool to about 40° C., add phase C, homogenize again.

Application Example 44
Skincare Cream, W/O Type
Phase A
6.00 PEG-7 hydrogenated castor oil
8.00 cetearyl octanoate
5.00 isopropyl myristate
15.00 mineral oil
2.00 PEG-45/dodecyl glycol copolymer
0.50 magnesium stearate
0.50 aluminum stearate
Phase B
3.00 glycerol
3.30 polymer according to Preparation Example 10
0.70 magnesium sulfate
2.00 panthenol
q.s. preservative
48.00 dist. water
Phase C
1.00 tocopherol
5.00 tocopheryl acetate
q.s. perfume oil Preparation:
Heat phases A and B separately to about 80° C. Stir phase B into phase A and homogenize. Cool to about 40° C., add Phase C and briefly homogenize again.

Application Example 45
Lipcare Cream
Phase A
10.00 cetearyl octanoate
5.00 polybutene
Phase B
0.10 carbomer
Phase C
2.00 ceteareth-6
2.00 ceteareth-25
2.00 glyceryl stearate
2.00 cetyl alcohol
1.00 dimethicone
1.00 benzophenone-3
0.20 bisabolol 6.00 mineral oil Phase D 8.00 polymer according to Preparation Example 33a 3.00 panthenol 3.00 propylene glycol q.s. preservative 54.00 dist. water Phase E 0.10 triethanolamine Phase F 0.50 tocopheryl acetate 0.10 tocopherol q.s. perfume oil Preparation:

Dissolve phase A until clear. Add phase B and homogenize. Add phase C and melt at 80° C. Heat phase D to 80° C. Add phase D to phase ABC and homogenize. Cool to about 40° C., add phase E and phase F, homogenize again.

Application Example 46

Glossy Lipstick

Phase A 5.30 candelilla (Euphorbia Cerifera) wax 1.10 beeswax 1.10 microcrystalline wax 2.00 cetyl palmitate 3.30 mineral oil 2.40 castor oil, glyceryl ricinoleate, octyldodecanol, carnauba, candelilla wax, 0.40 bisabolol 16.00 cetearyl octanoate 2.00 hydrogenated cocoglycerides q.s. preservative 1.00 polymer according to Preparation Example 33e 60.10 castor (Ricinus Communis) oil 0.50 tocopheryl acetate Phase B 0.80 C. I. 14 720:1, Acid Red 14 Aluminum Lake Phase C 4.00 mica, titanium dioxide Preparation:

Weigh in the components of phase A and melt. Incorporate phase B until homogeneous. Add phase C and stir in. Cool to room temperature with stirring.

We claim:

1. A method for improving the appearance or feel of skin or hair, said method comprising applying to the skin or hair a cosmetic composition obtained by free-radical graft copolymerization of a) at least one open-chain N-vinylamide compound of the formula (I)

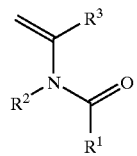

(I)

where $R^1$, $R^2$, $R^3$=H or $C_1$–$C_6$-alkyl, and b) optionally one or more further copolymerizable monomers to a polymeric graft base c), for cosmetic applications, with the proviso that if the polymeric graft base is a polyether-containing compound, the copolymerizable monomer b) is not a vinyl ester.

2. The method as claimed in claim 1, wherein the graft polymers are water-soluble or water-dispersible.

3. The method as claimed in claim 1, where the radicals $R^1$, $R^2$ and $R^3$ in formula (I)=H.

4. The method as claimed in claim 1, wherein c) is chosen from c1) polyether-containing compounds c2) polymers which contain at least 5% by weight of vinylpyrrolidone units c3) polymers which contain at least 50% by weight of vinyl alcohol units and/or c4) natural substances which contain saccharide structures.

5. The method as claimed in claim 4, wherein the polyether-containing compound c1) is chosen from polymers of the formula II having an average molecular weight of >300

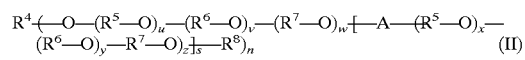

(II)

in which the variables, independently of one another, have the following meanings:

$R^4$ is hydrogen, $C_1$–$C_{24}$-alkyl, $R^9$—C(=O)—, $R^9$—NH—C(=O)—, polyalcohol radical;

$R^8$ is hydrogen, $C_1$–$C_{24}$-alkyl, $R^9$—C(=O)—, $R^9$—NH—C(=O)—;

$R^5$ to $R^7$ are —(CH$_2$)$_2$—, —(CH$_2$)$_3$—, —(CH$_2$)$_4$—, —CH$_2$—CH($R^9$)—, —CH$_2$—CHOR$^{10}$—CH$_2$—;

$R^9$ is $C_1$–$C_{24}$-alkyl;

$R^{10}$ is hydrogen, $C_1$–$C_{24}$-alkyl, $R^9$—C(=O)—, $R^9$—NH—C(=O)—;

A is —C(=O)—O, —C(=O)—B—C(=O)—O, —C(=O)—NH—B—NH—C(=O)—O;

B is —(CH$_2$)$_t$—, arylene, optionally substituted;

n is 1;

s is 0 to 1000;

t is 1 to 12;

u is 1 to 5000;

v is 0 to 5000;

w is 0 to 5000;

x is 0 to 5000;

y is 0 to 5000;

z is 0 to 5000.

6. The method as claimed in claim 5, wherein the polyether-containing compound c1) is chosen from polymers of the formula II having an average molecular weight of from 300 to 100,000 (according to the number average), in which the variables, independently of one another, have the following meanings:

$R^4$ is hydrogen, $C_1$–$C_{12}$-alkyl, $R^9$—C(=O)—, $R^9$—NH—C(=O)—, polyalcohol radical;

$R^8$ is hydrogen, $C_1$–$C_{12}$-alkyl, $R^9$—C(=O)—, $R^9$—NH—C(=O)—;

$R^5$ to $R^7$ are —(CH$_2$)$_2$—, —(CH$_2$)$_3$—, —(CH$_2$)$_4$—, —CH$_2$—CH($R^9$)—, —CH$_2$—CHOR$^{10}$—CH$_2$—;

$R^9$ is $C_1$–$C_{12}$-alkyl;

$R^{10}$ is hydrogen, $C_1$–$C_{12}$-alkyl, $R^9$—C(=O)—, $R^9$—NH—C(=O)—;

n is 1 to 8;

s is 0;

u is 2 to 2000;

v is 0 to 2000;

w is 0 to 2000.

7. The method as claimed in claim 5, wherein the polyether-containing compound c1) is chosen from polymers of the formula II having an average molecular weight of from 500 to 50,000 (according to the number average), in which the variables, independently of one another, have the following meanings:

$R^4$ is hydrogen, $C_1$–$C_6$-alkyl, $R^9$—C(=O)—, $R^9$—NH—C(=O)—;

$R^8$ is hydrogen, $C_1$–$C_6$-alkyl, $R^9$—C(=O)—, $R^9$—NH—C(=O)—;

$R^5$ to $R^7$ are —$(CH_2)_2$—, —$(CH_2)_3$—, —$(CH_2)_4$—, —$CH_2$—CH($R^9$)—, —$CH_2$—CHOR$^{10}$—$CH_2$—;

$R^9$ is $C_1$–$C_6$-alkyl;

$R^{10}$ is hydrogen, $C_1$–$C_6$-alkyl, $R^9$—C(=O)—, $R^9$—NH—C(=O)—;

s is 0;

u is 5 to 500;

v is 0 to 500;

w is 0 to 500.

8. The use of water-soluble or water-dispersible graft copolymers as claimed in claim 4, wherein the polyether-containing compound c1) is chosen from polyether-containing silicone derivatives.

9. The method as claimed in claim 4, wherein the polyether-containing compound c1) is chosen from polyether-containing silicone derivatives of the formula III (III)

$$R^{13}\!-\!\!\underset{\underset{R^{11}}{|}}{\overset{\overset{R^{11}}{|}}{Si}}\!-\!O\!\!\left[\!\underset{\underset{R^{11}}{|}}{\overset{\overset{R^{11}}{|}}{Si}}\!-\!O\!\right]_a\!\!\left[\!\underset{\underset{R^{11}}{|}}{\overset{\overset{R^{11}}{|}}{Si}}\!-\!O\!\right]_b\!\underset{\underset{R^{11}}{|}}{\overset{\overset{R^{11}}{|}}{Si}}\!-\!R^{12}$$

where:

$R^{12}$ and $R^{13}$ = $CH_3$ or $-\!\!\left[O\!\!-\!\!\!\underset{}{\overset{}{\phantom{X}}}\!\!-\!\!O\right]_c\!\!\left[O\!\!-\!\!\!\underset{}{\overset{CH_3}{\phantom{X}}}\!\!-\!\!O\right]_d\!\!R^{14}$ $R^{14}$ = H, $CH_3$, $-\!\!\left[\!\underset{\underset{R^{11}}{|}}{\overset{\overset{R^{11}}{|}}{Si}}\!-\!O\!\right]_a\!\!\underset{\underset{R^{11}}{|}}{\overset{\overset{R^{11}}{|}}{Si}}\!-\!CH_3$ or $-\!\!\left(\!\!\overset{\overset{O}{\|}}{C}\!\right)_e\!\!R^{15}$ $R^{14}$ = H, $CH_3$, $-\!\!\left[\!\underset{\underset{R^{11}}{|}}{\overset{\overset{R^{11}}{|}}{Si}}\!-\!O\!\right]_a\!\!\underset{\underset{R^{11}}{|}}{\overset{\overset{R^{11}}{|}}{Si}}\!-\!CH_3$ $-\!\!\left(\!\!\overset{\overset{O}{\|}}{C}\!\right)_e\!\!R^{15}$ $R^{15}$ is a $C_1$–$C_{40}$ organic radical which can contain amino, carboxylic acid or sulfonate groups, or for the case e=0, is also the anion of an inorganic acid, and where the radicals $R^{11}$ may be identical or different, and either originate from the group of aliphatic hydrocarbons having 1 to 20 carbon atoms, are cyclic aliphatic hydrocarbons having 3 to 20 carbon atoms, are of an aromatic nature or are identical to $R^{16}$, where:

$R^{16} = -\!\!(CH_2)_f\!\!-\!\!O\!\!-\!\!\!\underset{}{\overset{}{\phantom{X}}}\!\!-\!\!O\!\!\left[\!\!\underset{}{\overset{CH_3}{\phantom{X}}}\!\!-\!\!O\right]_d\!\!R^{14}$ with the proviso that at least one of the radicals $R^{11}$, $R^{12}$ or $R^{13}$ is a polyalkylene-oxide-containing radical according to the abovementioned definition, and f is an integer from 1 to 6, a and b are integers such that the molecular weight of the polysiloxane block is between 300 and 30 000, c and d may be integers between 0 and 50, with the proviso that the sum of c and d is greater than 0, and e is 0 or 1.

10. The method as claimed in claim 9, wherein formula III has the following meaning:

$$CH_3\!-\!\!\underset{\underset{R^{11}}{|}}{\overset{\overset{R^{11}}{|}}{Si}}\!-\!O\!\!\left[\!\underset{\underset{R^{11}}{|}}{\overset{\overset{R^{11}}{|}}{Si}}\!-\!O\!\right]_a\!\!\left[\!\underset{\underset{R^{16}}{|}}{\overset{\overset{R^{11}}{|}}{Si}}\!-\!O\!\right]_b\!\underset{\underset{CH_3}{|}}{\overset{\overset{CH_3}{|}}{Si}}\!-\!CH_3.$$

11. The method as claimed in claim 4, wherein the polyether-containing compound c1) is chosen from polymers obtained by reacting polyethyleneimines with alkylene oxides.

12. The method as claimed in claim 4, wherein the polyether-containing compounds c1) have been prepared by polymerization of ethylenically unsaturated alkylene-oxide-containing monomers and optionally further copolymerizable monomers.

13. The method as claimed in claim 12, wherein the polyether-containing compounds c1) have been prepared by polymerization of polyalkylene oxide vinyl ethers and optionally further copolymerizable monomers.

14. The method as claimed in claim 12, wherein the polyether-containing compounds c1) have been prepared by polymerization of polyalkylene oxide (meth)acrylates and optionally further copolymerizable monomers.

15. The method as claimed in claim 4, wherein the graft base c2), in addition to N-vinylpyrrolidone, further comprises a comonomer chosen from the group: N-vinylcaprolactam, N-vinylimidazole and alkyl-substituted N-vinylimidazoles and salts thereof with carboxylic acids or mineral acids, and quaternized products thereof, unsaturated sulfonic acids, diallylammonium chloride, vinyl esters, vinyl ethers, styrene, alkylstyrenes, monoethylenically unsaturated carboxylic acids and salts, esters, amides and nitriles thereof, maleic anhydride and its monoester, N,N-dialkylaminoalkyl (meth)acrylates, and salts thereof with carboxylic acids or mineral acids, and the quaternized products.

16. The method as claimed in claim 4, wherein the graft base c4) is chosen from monosaccharides, oligosaccharides, polysaccharides, oxidatively, hydrolytically or enzymatically degraded polysaccharides, chemically modified oligosaccharides or polysaccharides and mixtures thereof.

17. The method as claimed in claim 1, wherein the further comonomers b) are chosen from the group: monoethylenically unsaturated carboxylic acids and salts thereof, esters, amides and nitriles of monoethylenically unsaturated carboxylic acids, maleic anhydride and its monoester, diallylammonium chloride, vinyl esters, styrene, alkylstyrenes, unsaturated sulfonic acids, N-vinyllactams, vinyl ethers, 1-vinylimidazole and alkyl-substituted vinylimidazoles and salts thereof with carboxylic acids or mineral acids, and quaternized products thereof, N,N-dialkylaminoalkyl (meth)acrylates and quaternized products thereof.

18. The method as claimed in claim 1, wherein the polymers are at least partially saponified.

* * * * *